United States Patent
Phillips et al.

(10) Patent No.: US 12,390,236 B2
(45) Date of Patent: Aug. 19, 2025

(54) THROMBUS REMOVAL DEVICE

(71) Applicant: Covidien LP, Mansfield, MA (US)

(72) Inventors: Shawn Phillips, Belle Plaine, MN (US); Martin R. Willard, Burnsville, MN (US); Sarah E. Drilling, Minneapolis, MN (US); Alan M. Twomey, Minneapolis, MN (US); Wanda F. Dent, Chanhassen, MN (US); Nathan K. Weidenhamer, Minneapolis, MN (US)

(73) Assignee: Covidien LP, Mansfield, MA (US)

( * ) Notice: Subject to any disclaimer, the term of this patent is extended or adjusted under 35 U.S.C. 154(b) by 336 days.

(21) Appl. No.: 17/197,856

(22) Filed: Mar. 10, 2021

(65) Prior Publication Data
US 2022/0287729 A1    Sep. 15, 2022

(51) Int. Cl.
*A61B 17/221* (2006.01)
*A61B 17/22* (2006.01)

(52) U.S. Cl.
CPC ........ *A61B 17/221* (2013.01); *A61B 17/2202* (2013.01); *A61B 2017/22084* (2013.01); *A61B 2017/2212* (2013.01)

(58) Field of Classification Search
CPC .............. A61B 17/221; A61B 17/2202; A61B 2017/22084; A61B 2017/2212; A61B 17/3207
See application file for complete search history.

(56) References Cited

U.S. PATENT DOCUMENTS

| | | | |
|---|---|---|---|
| 4,728,319 | A | 3/1988 | Masch |
| 5,092,839 | A | 3/1992 | Kipperman |
| 5,549,626 | A | 8/1996 | Miller et al. |
| 5,766,191 | A | 6/1998 | Trerotola |
| 5,814,064 | A | 9/1998 | Daniel et al. |
| 5,817,104 | A | 10/1998 | Bilitz et al. |
| 6,001,118 | A | 12/1999 | Daniel et al. |
| 6,027,520 | A | 2/2000 | Tsugita et al. |
| 6,053,932 | A | 4/2000 | Daniel et al. |
| 6,059,796 | A | 5/2000 | Bilitz et al. |

(Continued)

FOREIGN PATENT DOCUMENTS

| | | |
|---|---|---|
| CA | 2603544 | 10/2006 |
| CN | 105377157 | 3/2016 |

(Continued)

OTHER PUBLICATIONS

U.S. Appl. No. 17/132,823, filed Dec. 23, 2020, naming inventors Twomey et al.

(Continued)

*Primary Examiner* — Sarah A Long
*Assistant Examiner* — James R McGinnity
(74) *Attorney, Agent, or Firm* — Shumaker & Sieffert, P.A.

(57) ABSTRACT

In some examples, a thrombus removal device includes a stationary element and a movable element configured to macerate a thrombus into smaller pieces as the thrombus moves into a basket defined by an expandable element. The stationary element defines a plurality of arms configured to segment the thrombus into smaller pieces. The movable element is configured to move relative to the stationary element, e.g., to rotate, plunge, vibrate, and/or oscillate, in order to macerate the thrombus.

20 Claims, 10 Drawing Sheets

(56) References Cited

U.S. PATENT DOCUMENTS

| | | | |
|---|---|---|---|
| 6,090,118 A | 7/2000 | McGuckin, Jr. |
| 6,093,196 A | 7/2000 | Okada |
| 6,152,946 A | 11/2000 | Broome et al. |
| 6,179,859 B1 | 1/2001 | Bates et al. |
| 6,221,006 B1 | 4/2001 | Dubrul et al. |
| 6,238,412 B1 | 5/2001 | Dubrul et al. |
| 6,245,089 B1 | 6/2001 | Daniel et al. |
| 6,258,115 B1 | 7/2001 | Dubrul |
| 6,361,545 B1 | 3/2002 | Macoviak et al. |
| 6,413,235 B1 | 7/2002 | Parodi |
| 6,454,775 B1 | 9/2002 | Demarais et al. |
| 6,468,291 B2 | 10/2002 | Bates et al. |
| 6,602,264 B1 | 8/2003 | McGuckin, Jr. |
| 6,652,548 B2 | 11/2003 | Evans et al. |
| 6,660,014 B2 | 12/2003 | Demarais et al. |
| 6,663,652 B2 | 12/2003 | Daniel et al. |
| 6,695,858 B1 | 2/2004 | Dubrul et al. |
| 6,699,260 B2 | 3/2004 | Dubrul et al. |
| 6,702,830 B1 | 3/2004 | Demarais et al. |
| 6,824,551 B2 | 11/2004 | Trerotola |
| 6,945,977 B2 | 9/2005 | Demarais et al. |
| 7,037,316 B2 | 5/2006 | McGuckin, Jr. et al. |
| 7,056,328 B2 | 6/2006 | Arnott |
| 7,108,704 B2 | 9/2006 | Trerotola |
| 7,137,991 B2 | 11/2006 | Fedie |
| 7,217,255 B2 | 5/2007 | Boyle |
| 7,220,269 B1 | 5/2007 | Andsel et al. |
| 7,354,445 B2 | 4/2008 | Nicholson |
| 7,507,246 B2 | 3/2009 | McGuckin et al. |
| 7,645,261 B2 | 1/2010 | Hinchliffe |
| 7,655,016 B2 | 2/2010 | Demarais et al. |
| 7,691,123 B2 | 4/2010 | Tsugita et al. |
| 7,819,887 B2 | 10/2010 | McGuckin, Jr. et al. |
| 7,909,801 B2 | 3/2011 | Hinchliffe |
| 7,955,345 B2 | 6/2011 | Kucharczyk et al. |
| 8,062,258 B2 | 11/2011 | Demarais et al. |
| 8,062,317 B2 | 11/2011 | McGuckin, Jr. et al. |
| 8,092,395 B2 | 1/2012 | Lupton et al. |
| 8,277,470 B2 | 10/2012 | Demarais et al. |
| 8,366,735 B2 | 2/2013 | Bose |
| 8,414,543 B2 | 4/2013 | McGuckin, Jr. et al. |
| 8,435,218 B2 | 5/2013 | Hinchliffe |
| 8,449,566 B2 | 5/2013 | Finitsis |
| 8,465,511 B2 | 6/2013 | McGuckin, Jr. et al. |
| 8,480,697 B2 | 7/2013 | Kucharczyk et al. |
| 8,545,447 B2 | 10/2013 | Demarais et al. |
| 8,603,122 B2 | 12/2013 | Pokorney et al. |
| 8,647,359 B2 | 2/2014 | Broome et al. |
| 8,784,434 B2 | 7/2014 | Rosenbluth et al. |
| 8,801,748 B2 * | 8/2014 | Martin ............... A61B 17/221 |
| | | 606/113 |
| 8,828,022 B2 | 9/2014 | White et al. |
| 8,968,330 B2 | 3/2015 | Rosenbluth et al. |
| 9,017,294 B2 | 4/2015 | McGuckin, Jr. et al. |
| 9,126,016 B2 | 9/2015 | Fulton |
| 9,149,609 B2 | 10/2015 | Ansel et al. |
| 9,186,487 B2 | 11/2015 | Dubrul et al. |
| 9,259,237 B2 | 2/2016 | Quick et al. |
| 9,387,098 B2 | 7/2016 | Ferrera et al. |
| 9,408,620 B2 | 8/2016 | Rosenbluth et al. |
| 9,427,252 B2 | 8/2016 | Sos |
| 9,439,664 B2 | 9/2016 | Sos |
| 9,474,543 B2 | 10/2016 | McGuckin, Jr. et al. |
| 9,498,604 B2 | 11/2016 | Dubrul et al. |
| 9,561,094 B2 | 2/2017 | Fulton |
| 9,700,332 B2 | 7/2017 | Marchand et al. |
| 9,827,084 B2 | 11/2017 | Bonnette et al. |
| 9,844,387 B2 | 12/2017 | Marchand et al. |
| 9,913,741 B2 | 3/2018 | Melsheimer et al. |
| 9,924,957 B2 | 3/2018 | McGuckin, Jr. et al. |
| 9,924,958 B2 | 3/2018 | Martin et al. |
| 9,943,397 B2 | 4/2018 | Bonnette et al. |
| 9,987,028 B2 | 6/2018 | Lowinger et al. |
| 10,045,790 B2 | 8/2018 | Cox et al. |
| 10,070,878 B2 | 9/2018 | Ma |
| 10,085,760 B2 | 10/2018 | Imai et al. |
| 10,092,324 B2 | 10/2018 | Gillespie et al. |
| 10,098,651 B2 | 10/2018 | Marchand et al. |
| 10,117,671 B2 | 11/2018 | McGuckin, Jr. et al. |
| 10,123,803 B2 | 11/2018 | Ferrera et al. |
| 10,231,751 B2 * | 3/2019 | Sos ..................... A61F 2/013 |
| 10,307,177 B2 | 6/2019 | Bonneau |
| 10,342,571 B2 | 7/2019 | Marchand et al. |
| 10,448,969 B2 | 10/2019 | Sutton et al. |
| 10,524,811 B2 | 1/2020 | Marchand et al. |
| 10,588,655 B2 | 3/2020 | Rosenbluth et al. |
| 10,743,907 B2 | 8/2020 | Bruzzi et al. |
| 10,779,852 B2 | 9/2020 | Bruzzi et al. |
| 11,464,537 B2 | 10/2022 | Cartier et al. |
| 11,529,158 B2 | 12/2022 | Hauser |
| 2002/0004667 A1 | 1/2002 | Adams et al. |
| 2003/0150821 A1 | 8/2003 | Bates |
| 2003/0153943 A1 | 8/2003 | Michael et al. |
| 2004/0138694 A1 | 7/2004 | Tran et al. |
| 2005/0159770 A1 | 7/2005 | Divani et al. |
| 2006/0224179 A1 | 10/2006 | Kucharczyk |
| 2007/0135832 A1 | 6/2007 | Wholey et al. |
| 2008/0033467 A1 | 2/2008 | Miyamoto et al. |
| 2008/0091223 A1 | 4/2008 | Pokorney |
| 2009/0198269 A1 | 8/2009 | Hannes et al. |
| 2009/0209831 A1 | 8/2009 | Kucharczyk |
| 2009/0292307 A1 | 11/2009 | Razack |
| 2010/0268264 A1 * | 10/2010 | Bonnette .......... A61B 17/22012 |
| | | 606/200 |
| 2010/0318097 A1 | 12/2010 | Ferrera et al. |
| 2011/0160741 A1 | 6/2011 | Asano et al. |
| 2011/0196414 A1 | 8/2011 | Porter et al. |
| 2011/0230908 A1 | 9/2011 | Finitsis |
| 2011/0230909 A1 | 9/2011 | Kucharczyk |
| 2012/0197276 A1 | 8/2012 | Lupton et al. |
| 2012/0239064 A1 | 9/2012 | Cartier et al. |
| 2013/0204351 A1 | 8/2013 | Cox et al. |
| 2014/0005714 A1 | 1/2014 | Quick et al. |
| 2014/0046243 A1 * | 2/2014 | Ray ..................... A61B 17/22 |
| | | 604/22 |
| 2014/0094841 A1 | 4/2014 | Sutton et al. |
| 2014/0236219 A1 | 8/2014 | Dubrul et al. |
| 2014/0303667 A1 | 10/2014 | Cox et al. |
| 2014/0303719 A1 | 10/2014 | Cox et al. |
| 2015/0025555 A1 | 1/2015 | Sos |
| 2015/0238207 A1 * | 8/2015 | Cox ..................... A61B 17/221 |
| | | 606/159 |
| 2015/0265299 A1 | 9/2015 | Cooper et al. |
| 2015/0297251 A1 | 10/2015 | Sos |
| 2015/0351770 A1 | 12/2015 | Fulton, III |
| 2015/0351775 A1 | 12/2015 | Fulton, III |
| 2016/0022293 A1 | 1/2016 | Dubrul et al. |
| 2016/0030155 A1 | 2/2016 | Cox et al. |
| 2016/0038174 A1 | 2/2016 | Bruzzi et al. |
| 2016/0067444 A1 | 3/2016 | Allen et al. |
| 2016/0106446 A1 | 4/2016 | Welch et al. |
| 2016/0206344 A1 | 7/2016 | Bruzzi et al. |
| 2016/0220346 A1 | 8/2016 | Bonnette et al. |
| 2016/0256180 A1 | 9/2016 | Vale et al. |
| 2016/0262790 A1 | 9/2016 | Rosenbluth et al. |
| 2017/0105745 A1 | 4/2017 | Rosenbluth et al. |
| 2018/0206865 A1 | 7/2018 | Martin et al. |
| 2018/0256177 A1 | 9/2018 | Cooper et al. |
| 2018/0256178 A1 | 9/2018 | Cox et al. |
| 2018/0271547 A1 | 9/2018 | Ulm, III |
| 2018/0361116 A1 | 12/2018 | Quick et al. |
| 2019/0046219 A1 | 2/2019 | Marchand et al. |
| 2019/0183519 A1 * | 6/2019 | Imai ............... A61B 17/320725 |
| 2019/0231373 A1 | 8/2019 | Quick |
| 2019/0239907 A1 * | 8/2019 | Brady ............ A61B 17/22031 |
| 2019/0321071 A1 | 10/2019 | Marchand et al. |
| 2020/0039745 A1 | 2/2020 | Khodl et al. |
| 2020/0046368 A1 | 2/2020 | Merritt et al. |
| 2020/0155293 A1 | 5/2020 | Morrison et al. |
| 2020/0397452 A1 | 12/2020 | Twomey et al. |
| 2022/0000505 A1 | 1/2022 | Hauser |
| 2022/0000506 A1 | 1/2022 | Hauser |
| 2022/0000507 A1 | 1/2022 | Hauser |
| 2022/0125451 A1 | 4/2022 | Hauser |

(56) References Cited

U.S. PATENT DOCUMENTS

FOREIGN PATENT DOCUMENTS

| | | | |
|---|---|---|---|
| CN | 105662647 A | 6/2016 |
| CN | 105852933 A | 8/2016 |
| CN | 106420004 A | 2/2017 |
| CN | 107212914 A | 9/2017 |
| CN | 110338878 A | 10/2019 |
| CN | 110495926 A | 11/2019 |
| DE | 602005025982 | 3/2011 |
| DE | 202013009532 | 11/2013 |
| EP | 1350473 | 10/2003 |
| EP | 1727584 | 12/2006 |
| EP | 2319575 A1 | 5/2011 |
| EP | 1871455 | 12/2014 |
| EP | 2967614 | 11/2016 |
| EP | 3364891 | 8/2018 |
| EP | 3539486 | 9/2019 |
| EP | 3003175 | 8/2020 |
| JP | 2011101674 | 5/2011 |
| JP | 4731471 B2 | 7/2011 |
| JP | 5805736 B2 | 11/2015 |
| WO | 1996/23446 | 8/1996 |
| WO | 99/23952 A1 | 5/1999 |
| WO | 2000/53120 | 9/2000 |
| WO | 2004/093966 A1 | 11/2004 |
| WO | 2006107641 | 10/2006 |
| WO | 2009/055782 A1 | 4/2009 |
| WO | 2009/077203 | 6/2009 |
| WO | 2011/82319 A1 | 7/2011 |
| WO | 2012/09675 A2 | 1/2012 |
| WO | 2014141226 | 9/2014 |
| WO | 2015/187196 A1 | 12/2015 |
| WO | 2015183338 | 12/2015 |
| WO | 2017/070702 A2 | 4/2017 |
| WO | 2017/074530 | 5/2017 |

OTHER PUBLICATIONS

Extended Search Report from counterpart European Application No. 22158951.8 dated Jun. 22, 2022, 8 pp.

Response to Extended Search Report dated Jun. 30, 2022, from counterpart European Application No. 22158951.8 filed Feb. 22, 2023, 14 pp.

Communication pursuant to Article 94(3) EPC from counterpart European Application No. 22158951.8 dated Oct. 19, 2023, 4 pp.

Response to Communication pursuant to Article 94(3) EPC dated Oct. 19, 2023, from counterpart European Application No. 22158951.8 filed Feb. 16, 2024, 12 pp.

* cited by examiner

THROMBUS REMOVAL DEVICE

TECHNICAL FIELD

The disclosure relates to removal of occlusive material from vasculature of a patient.

BACKGROUND

In some medical procedures, a thrombus or other occlusive material is removed from a body lumen (e.g., a blood vessel) to maintain the patency of the body lumen. When the thrombus is in the vasculature of a patient, removal of at least part of the thrombus from the vasculature can alleviate symptoms associated with the occlusion or help prevent the thrombus from dislodging, moving through the bloodstream, and creating an embolism, e.g., a pulmonary embolism.

SUMMARY

This disclosure describes example thrombus removal devices that include an expandable element, a stationary element configured to segment a thrombus into smaller pieces as the stationary element moves through the thrombus, and a movable element disposed radially inward from the stationary element, wherein the movable element is configured to macerate the thrombus. The expandable element, the stationary element, and the movable element are configured to expand radially outward from a delivery configuration to a deployed configuration. In the deployed configuration, the movable element is configured to move (e.g., rotate, plunge, and/or vibrate) relative to the stationary element in order to macerate the thrombus. In some examples, the thrombus removal device is configured to be moved proximally through a thrombus while in the deployed configuration in order to collect at least part of the thrombus in a basket of the expandable element.

In a first example, a medical device includes an elongated support member; an expandable element disposed on the elongated support member, a stationary element comprising a plurality of arms, wherein the plurality of arms is configured to segment a thrombus into smaller pieces as the thrombus moves through the stationary element, wherein the expandable element is configured to capture at least some of the smaller pieces; and a movable element disposed radially inward from the stationary element, the movable element configured to move relative to the stationary element to macerate the thrombus as the thrombus moves through the stationary element.

In another example, a medical device includes an elongated support member; an expandable element disposed on the elongated support member, wherein the elongated support member is positioned generally along a longitudinal axis extending from a proximal end of the expandable element to a distal end of the expandable element, and wherein the distal end of the expandable element is slidably coupled to the elongated support member; a stationary element comprising a plurality of arms, wherein the plurality of arms is configured to segment a thrombus into smaller pieces as the thrombus moves through the stationary element, wherein the expandable element is configured to capture at least some of the smaller pieces; and a movable element disposed radially inward from the stationary element, the movable element configured to move relative to the stationary element to macerate the thrombus as the thrombus moves through the stationary element.

In another example, a system includes a medical device having an elongated support member; an expandable element disposed on the elongated support member, wherein the elongated support member is positioned generally along a longitudinal axis extending from a proximal end of the expandable element to a distal end of the expandable element, and wherein the distal end of the expandable element is slidably coupled to the elongated support member; a stationary element comprising a plurality of arms, wherein the plurality of arms is configured to segment a thrombus into smaller pieces as the thrombus moves through the stationary element, wherein the expandable element is configured to capture at least some of the smaller pieces; and a movable element disposed radially inward from the stationary element, the movable element configured to move relative to the stationary element to macerate the thrombus as the thrombus moves through the stationary element; an actuator configured to control a motion of the movable element; and a delivery catheter defining a delivery catheter inner lumen, wherein the medical device is configured to be received in the delivery catheter inner lumen when the expandable element is in the delivery configuration.

In another example, a method includes using a medical device to macerate a thrombus, wherein the medical device includes an elongated support member; an expandable element disposed on the elongated support member, wherein the elongated support member is positioned generally along a longitudinal axis extending from a proximal end of the expandable element to a distal end of the expandable element, and wherein the distal end of the expandable element is slidably coupled to the elongated support member; a stationary element comprising a plurality of arms, wherein the plurality of arms is configured to segment a thrombus into smaller pieces as the thrombus moves through the stationary element, wherein the expandable element is configured to capture at least some of the smaller pieces; and a movable element disposed radially inward from the stationary element, the movable element configured to move relative to the stationary element to macerate the thrombus as the thrombus moves through the stationary element.

The details of one or more examples are set forth in the accompanying drawings and the description below. Other features, objects, and advantages will be apparent from the description and drawings, and from the claims.

DETAILED DESCRIPTION

Figure 1:
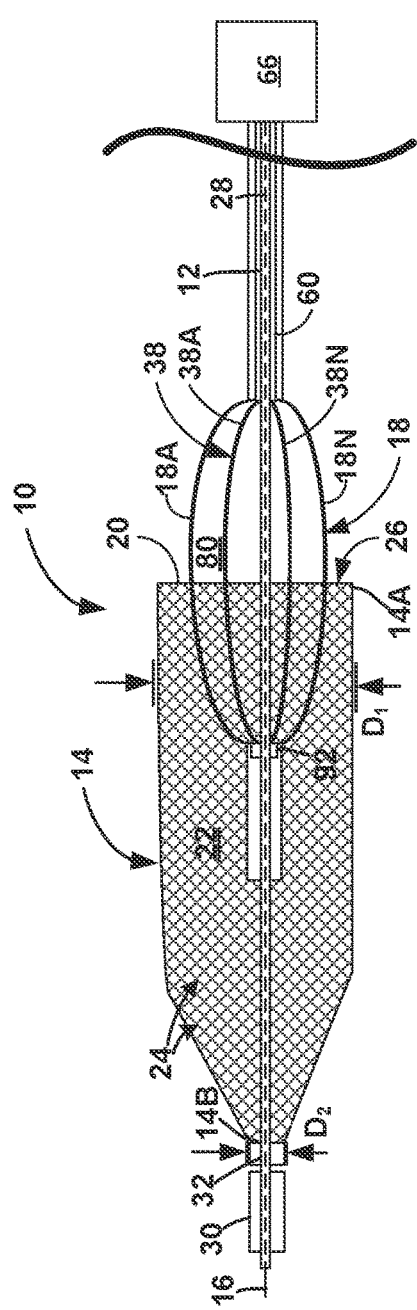
FIG. 1 is a conceptual side elevation view of an example thrombus removal device.

Thrombus removal devices described herein (also referred to herein as thrombus collection devices) are configured to remove occlusive material (e.g., a thrombus, an embolus, fatty deposits, and the like) from vasculature of a patient during an endovascular procedure or to remove occlusive material from other hollow anatomical structures of a patient. Example thrombus removal devices described herein include an expandable element configured to capture occlusive material from the vasculature of a patient, and a movable element disposed radially inward from a stationary element, wherein the movable element and stationary element are configured to segment the occlusive material into smaller pieces as the stationary and movable elements move through the occlusive material. Segmenting the occlusive material into smaller pieces may help prevent larger pieces of the occlusive material from dislodging and moving downstream in the blood flow, which may create an embolism. While a thrombus and blood vessels/vasculature are primarily referred to throughout the remainder of the disclosure, it should be understood that the thrombus removal devices and techniques described herein can be used to collect and remove other types of occlusive material from a hollow anatomical structure of a patient.

Example thrombus removal devices described herein include an expandable element, an elongated expandable element support structure, a stationary element, and a movable element configured to expand radially outward from a delivery configuration to a deployed configuration. In some examples, any or all of the expandable element, the stationary element, and the movable element are configured to self-expand. For example, any or all of the expandable element, the stationary element, and the movable element may be formed from a self-expanding structure, such as a laser-cut nitinol frame or another self-expandable frame. In other examples, the any or all of the expandable element, the stationary element, and the movable element are configured to be manually expanded from the delivery configuration to the deployed configuration by a clinician, e.g., using a push wire, a pull wire, or another actuation mechanism connected to the respective structure. In other examples, any or all of the expandable element the stationary element, and the movable element may include a combination thereof, such as a laser-cut nitinol frame coupled to a manual expansion mechanism.

In the deployed configuration, the expandable element defines a proximal mouth configured to receive a thrombus and a basket configured to receive at least part of the thrombus after it has moved through the proximal mouth. The basket has a closed end to retain the collected thrombus pieces. The stationary element defines a plurality of arms configured to segment the thrombus into smaller pieces as the stationary element moves through the thrombus. For example, the plurality of arms may be relatively rigid and configured to cut through the thrombus as the stationary element is moved proximally through the thrombus and as the thrombus is pushed past the arms and into the distal basket of the expandable element. The basket is configured to retain and hold these smaller pieces of the thrombus, thereby preventing at least part of the thrombus from moving downstream in the blood flow.

The stationary element may define any suitable number of stationary elongated arms, such as, but not limited to two arms to six arms, or about three arms. In addition, the stationary element may have any suitable length, such as, but not limited to, a length of about 50 millimeters (mm) to about 150 mm, measured from a proximal-most end of the stationary element (e.g., at a proximal end of the arms) to a distal-most end of the stationary element (e.g., at a distal end of the arms). In some examples, such as when used to describe numerical values, "about" or "approximately" refers to a range within the numerical value resulting from manufacturing tolerances and/or within 1%, 5%, or 10% of the numerical value. For example, a length of about 10 mm refers to a length of 10 mm to the extent permitted by manufacturing tolerances, or a length of 10 mm+/−0.1 mm, +/−0.5 mm, or +/−1 mm in various examples.

The movable element is disposed radially inward from (e.g., within a volume defined by) the stationary element and is configured to move relative to the stationary element to break down (e.g., fragment or macerate) as the thrombus comes into contact with the movable element. For example, the stationary element may segment the thrombus into smaller pieces and the movable element may segment these thrombus pieces into even smaller pieces to facilitate capture in the basket defined by the expandable element. The movable element may define any suitable structural configuration. For example, the movable element may define one or more movable elongated arms configured to move relative to the stationary element (e.g., rotate, vibrate, and/or plunge) in order to macerate the thrombus. The movable element may define any suitable number of movable arms, such as, but not limited to one arm to six arms. The one or more elongated arms may be connected to an elongated movable element support structure that is configured to transfer a movement (e.g., rotation, vibration, or plunging movement) to the movable element from a device at a proximal portion of the thrombus removal device. The movable element support structure can be, for example, a tube that is positioned radially outward of an expandable element support structure to which the expandable element is connected.

The movable element may have any suitable length, such as, but not limited to, a length of about 50 mm to about 150 mm, measured from a proximal-most end of the movable element (e.g., at a proximal end of the one or more movable arms) to a distal-most end of the movable element (e.g., at a distal end of the one or more movable arms).

A movable element configured to macerate a thrombus may enable the thrombus removal device to have a shorter configuration (e.g., as measured along a central longitudinal axis of the device) compared to otherwise like-configured thrombus removal devices that do not include a movable element. In addition, the movable element may reduce the duration of a thrombus removal procedure by enabling a larger percentage of a thrombus to be collected during one "pass" of the thrombus removal device through the thrombus, thereby reducing a number of device-insertion sessions for a given thrombus. During some thrombus removal procedures, the thrombus removal device may be introduced into the vasculature of a patient, passed through a thrombus to collect part of the thrombus in the expandable element of the thrombus removal device, and then subsequently removed from the patient and cleaned to remove at least some of the collected thrombus. Thereafter, the thrombus removal device may be reintroduced into the vasculature and the process may be repeated one or more times until a sufficient amount of the thrombus is removed from the patient using the thrombus removal device. Each of these iterations may be referred to as a "pass" through the thrombus.

In some examples, in its deployed configuration, a proximal portion of the expandable element (e.g., a circumference of the proximal mouth) is configured to substantially conform (e.g., conform or nearly conform) to a shape of an inner wall of a blood vessel. When the expandable element is selected to be oversized relative to an intended blood vessel, the proximal portion of the expandable element is configured to be in apposition with a vessel wall. This configuration may help the proximal mouth of the expandable element stay open, and in some cases, centered in the vessel, as a thrombus moves distally into the basket of the expandable element, and may help enable a relatively large percentage of the thrombus to be collected in the basket of the expandable element. In some examples, the expandable member is also configured to self-center due at least in part to one or more of a radially symmetric design or being self-expandable. In some examples, the proximal mouth of the expandable element is configured to have an outward radial force greater than the radial force of the basket of the expandable element. In addition, in some examples, when the expandable element is in its deployed configuration, the proximal mouth of the expandable element is configured to have an outward radial force greater than the radial force of the basket of the expandable element. The radially outward biasing force of the stationary element and/or the movable element may contribute to the outward radial force of the proximal mouth of the expandable element because the stationary element and the movable element are positioned proximate the proximal mouth and closer to the proximal end of the expandable element than the distal end.

In some examples, in the deployed configuration, the expandable element tapers in a distal direction along a majority of a length of at least the distal portion of the expandable element, such as along a majority of a length of the distal basket or along a majority of the length of the entire expandable element. The taper can be, for example, a constant taper, a stepped taper, or a gradual taper, and can define a conical-shaped distal basket. In some examples, the expandable element tapers from a diameter of about 20 mm at the proximal mouth to a diameter of 2 mm at the distal end. As a result of the tapering configuration, only a relatively small length of the expandable element is configured to contact the inner wall of the blood vessel when the expandable element is deployed within the blood vessel, which may help reduce adverse impact the expandable element has on the wall of the blood vessel as a clinician pulls the expandable element proximally through the blood vessel and through the clot.

In addition, due to the distal taper of the expandable element and the corresponding decrease in volume in the basket of the expandable element in the distal direction, the expandable element as configured compresses the thrombus positioned in the basket as the expandable element is proximally withdrawn into a retrieval catheter. Compressing the thrombus may expel water from the thrombus and further dehydrate the thrombus, such that it decreases in volume in the basket, which may help aid retrieval of the thrombus removal device with a relatively small profile catheter. The tapered shape of the expandable element may also help distribute the thrombus longitudinally within the basket as the expandable element is proximally withdrawn into a retrieval catheter, which may help mitigate the possibility of having too much relatively rigid material (e.g., the macerated thrombus) at the distal-most end of the basket. A relatively large bulk of relatively rigid material at the distal-most end of the basket may interfere with the proximal withdrawal of the thrombus removal device into a retrieval catheter.

The basket of the expandable element defines a plurality of openings, e.g., a mesh, configured to enable fluid to flow through the basket while still retaining collected pieces of thrombus in the distal basket. In some examples, the size of the openings may be constant throughout the basket, while in other examples, the average size of the openings may decrease from a proximal end to a distal end of the basket to help prevent escape of collected thrombus during retrieval of the thrombus removal device from a patient.

In some existing techniques, occlusive material lodged within a blood vessel of a patient may be removed by delivering a chemical substance (e.g., a lytic agent) or by aspirating the occlusive material from the blood vessel. While these techniques may be useful, they may also result in relatively large particulate debris breaking off from the thrombus, flowing downstream of the treatment site, and potentially restricting downstream blood flow. A filter or other device may be used to try to capture the particulate debris, but there may be design challenges to placing the filter for successful removal of the occlusive material while capturing any particulate debris from flowing downstream of the treatment site. In contrast to a more passive filter that may catch particulate in a blood stream, the thrombus removal devices described herein are configured to more actively capture a thrombus, e.g., by segmenting the thrombus into smaller pieces via the stationary element and the movable element, and capturing the smaller pieces in a basket as a clinician moves an expandable element of the respective thrombus removal device proximally through the thrombus.

Further, in contrast to systems that primarily rely on delivery of a chemical substance or the application of aspiration to a thrombus, the thrombus removal devices described herein may require less capital equipment and may be less cumbersome to operate. For example, the thrombus removal devices may be delivered to a treatment site within vasculature with the aid of a relatively straightforward catheter assembly (e.g., including a guidewire and one or more catheters) and may not require a separate vacuum device or therapeutic agent delivery device. In some examples, however, the thrombus removal devices described herein may be used in combination with delivery of a chemical substance (e.g., a lytic agent) to a thrombus and/or aspiration of the thrombus.

The elongated expandable element support structure of the thrombus removal device may be used to deliver and control the position of the expandable element in the vasculature of the patient from a location outside of the patient. For example, the elongated expandable element support structure may have the configuration of a guidewire or another elongated body. In some examples, the elongated expandable element support structure extends through the expandable element from a proximal end of the expandable element to a distal end of the expandable element. In other examples, the elongated expandable element support structure may not extend through the expandable element from a proximal end of the expandable element to a distal end of the expandable element, and may terminate at the proximal portion (e.g., at the proximal end) of the expandable element. In these examples, the distal portion of the expandable element may not be connected to any elongated element. That is, the distal portion of the expandable element is either mechanically connected to the elongated expandable element support structure or is not mechanically connected to any elongated expandable element support structure extending through the expandable element from a proximal end of the expandable element to a distal end of the expandable element. In any of these examples, however, a guidewire may be used with the thrombus removal device and may extend through the expandable element during use of the thrombus removal device.

In some examples, the distal portion of the expandable element is configured to move longitudinally relative to the elongated expandable element support structure and move towards or away from the proximal portion of the expandable element. This may be useful for maintaining apposition of the proximal portion of the expandable element with a vessel wall, as well as accommodating the change in expandable element dimensions as a thrombus is collected in the basket defined by the distal portion of the expandable element and/or as the expandable element is proximally withdrawn into a catheter lumen. In other examples, the distal portion of the expandable element is fixed relative to the proximal end of the expandable element.

FIG. 1 is a side view of an example thrombus removal device 10, which is configured to remove occlusive material within vasculature of a patient. Although FIG. 1, as well as many of the other figures are referred to herein as "side views," in some cases, portions of the devices are removed to show, for example, an inner lumen or the like. Thus, the side views may also be referred to as conceptual cross-sectional views in some cases. The thrombus removal device 10 can be used with any suitable treatment procedure. For example, the thrombus removal device 10 can be used to remove a thrombus from within iliofemoral veins, central veins, upper extremity veins, peripheral large arteries, arteriovenous fistulae, or any other suitable target site within a patient.

The thrombus removal device 10 includes an elongated expandable element support structure 12, an expandable element 14 disposed on the expandable element support structure 12, a stationary element 18, and a movable element 38 connected to a movable element support structure 60. The expandable element support structure 12 is fixedly connected to the expandable element 14 using any suitable technique. In some examples, the expandable element 14 may be connected to the expandable element support structure 12 by an adhesive, solder, welding, crimped elements, such as bands or beads, and other suitable fixation mechanisms and/or elements or combinations thereof. In other examples, the expandable element 14 may be formed directly onto the expandable element support structure 12, such as by incorporating one or more sections of the expandable element support structure 12 into a material forming the expandable element 14.

The expandable element support structure 12 provides a structure by which a clinician may control the expandable element 14. For example, a clinician may grasp and manipulate a proximal portion of the expandable element support structure 12 to deploy the expandable element 14 from a delivery catheter and directly into a blood vessel of a patient, to move the expandable element 14 through a thrombus in the blood vessel, and to remove the expandable element 14 from the blood vessel. The expandable element support structure 12 may have any suitable length, such as, but not limited to, about 50 centimeters (cm) to about 100 cm, such as about 60 cm, about 75 cm, or about 90 cm (e.g., exactly these lengths or approximately these lengths to the extent permitted by manufacturing tolerances), and may be formed from any suitable material. For example, the expandable element support structure 12 may be formed from a metal, a polymer, or combinations thereof. Example materials for the expandable element support structure 12 include, but are not limited to, nitinol (nickel titanium), stainless steel, cobalt-chromium-nickel molybdenum-iron alloy (e.g., commercially available under the trade designation Elgiloy™ available from Elgiloy Specialty Metals of Elgin, Illinois), carbon fiber and its composites, and engineered polymers such as liquid crystal polymers, polyether ether ketone (PEEK), polyamide, polyimide, polyester, and the like.

The expandable element support structure 12 is sufficiently flexible to enable the thrombus removal device 10 to be navigated through the vasculature, which may be relatively tortuous in some cases, without kinking or becoming arrested by the vasculature en route to the treatment site. The expandable element support structure 12 may be solid in some examples, or may be hollow over some or all of its length. For example, in the example shown in FIG. 1, the expandable element support structure 12 defines an inner lumen configured to receive a guidewire 16. During use of the thrombus removal device 10 in a patient, the guidewire 16 may be extended along a full length of the expandable element support structure 12 or may extend only along a portion of the expandable element support structure 12, e.g., in a rapid exchange-type configuration, and may be used to aid delivery of the thrombus removal device 10 to a treatment site within the vasculature of a patient.

In some examples, the expandable element support structure 12 may include a lumen and a plurality of holes (not shown) through which a physician may infuse or release a lytic agent to dissolve the thrombus 36. In other examples, the physician may infuse a lytic agent from another component of the thrombus removal device 10, such as from a lumen of a movable element support structure 60, e.g., from between the movable element support structure 60 and the expandable element support structure 12, from a delivery catheter configured to deliver the thrombus removal device 10 to a target site within vasculature of a patient, from a retrieval catheter used to retrieve the thrombus removal device 10 from the target site, or any combination thereof.

In some examples, the expandable element 14 is configured to elongate and constrict in the longitudinal direction and/or expand in a radially outward direction. For example, the expandable element 14 can be fixedly connected to a distal slider 32. The distal slider 32 is configured to move relative to a proximal end 14A of the expandable element 14, such as by sliding along an outer surface of the expandable element support structure 12. In some examples, the distal slider 32 has a tubular body or a partial-ring shape that fits around the outer surface of the expandable element support structure 12.

In some examples, the expandable element support structure 12 may include at least one mechanical stop that limits the relative proximal and distal sliding of the distal slider 32 of the expandable element 14. The ability of the expandable element distal end 14B to move relative to the expandable element proximal end 14A and relative to the expandable element support structure 12 may enable the expandable element 14 to conform to the inner wall of the peripheral vasculature while the expandable element support structure 12 is moving through the thrombus, during deployment, or retrieval of the expandable element support structure 12. For example, a clinician can slide the expandable element distal end 14B proximally or distally relative to the proximal end 14A of the expandable element 14 so that the expandable element 14 more-closely adheres to the inner wall of a blood vessel. In other examples, the expandable element 14 may be fixed to the expandable element support structure 12, such as by welding, adhesive, a mechanical connection, e.g., crimping a part of the expandable element 14 to the expandable element support structure 12.

The expandable element 14 is configured to expand radially outward from a relatively low profile (e.g., relatively small radial profile) delivery configuration to an expanded deployed configuration. In some examples, the expandable element 14 is configured to self-expand from the delivery configuration to the deployed configuration, e.g., in response to being released from an inner lumen of a delivery catheter. The compressive force applied to the expandable element 14 by the delivery catheter when the expandable element 14 is in the inner lumen may help hold the expandable element 14 in the delivery configuration. When the expandable element 14 is deployed from the inner lumen of the delivery catheter, the expandable element 14 may self-expand radially outward into its deployed configuration. In self-expanding examples, the expandable element 14 may be formed from any suitable material, such as, but not limited to, nitinol. For example, the expandable element 14 may be formed from a cut (e.g., a laser-cut) nitinol tube, e.g., similar to a stent, or from a nitinol mesh. A nitinol structure can be heat-set to assume a desired shape upon deployment within a patient.

In other examples, however, the expandable element 14 is not configured to self-expand and instead may be expanded with the aid of an expansion mechanism, such as, but not limited to, a balloon positioned inside an interior space of the expandable element 14 or via another actuation mechanism, such as a push or pull wire, connected to the expandable element 14. In these examples, the expandable element 14 may be formed from any suitable material, such as, but not limited to, stainless steel or a polymeric material.

The expandable element 14 may be configured to assume a delivery configuration that enables the expandable element 14 to be delivered to a target site within vasculature of a patient using a relatively small profile delivery catheter, such as, but not limited to, an 8 French (Fr) catheter to a 12 Fr catheter, or another catheter having an outer diameter of less than or equal to about 4 mm. A relatively small profile delivery catheter may permit the catheter to pass distally through a thrombus 36 (FIG. 2) to deploy the expandable element 14 on a distal side of the thrombus without creating large thrombus debris during the movement distally through the thrombus. As discussed below, a clinician may deploy the expandable element 14 from the delivery catheter on the distal side of the thrombus and withdraw the expandable element 14 proximally through the thrombus to capture at least part of the thrombus in the expandable element 14. In addition, relatively small profile delivery catheter may reduce interaction between the delivery catheter and one or more other medical devices implanted in the vasculature of the patient, such as an inferior vena cava (IVC) filter.

In the deployed configuration, the expandable element proximal end 14A defines a proximal mouth 20 configured to receive a thrombus, and the expandable element 14 defines a basket 22 configured to receive at least part of the thrombus after it has moved through the proximal mouth 20. The proximal mouth 20 may also be referred to as a "proximal-facing mouth" in some examples, because it provides an opening to the expandable element 14 in the proximal direction. The basket 22 has a closed distal end 14B configured to retain at least part of the collected thrombus pieces.

Regardless of whether the expandable element 14 is configured to self-expand, the expandable element 14 may be formed from any material that is suitably flexible and resilient to enable the expandable element proximal portion 14A to substantially conform to (e.g., conform or nearly conform to) a wall of a blood vessel 34 (FIG. 2) when the expandable element 14 is deployed within the blood vessel. As discussed in further detail below, substantially conforming the basket 22 to the wall of a blood vessel may better enable the expandable element 14 to capture thrombi (e.g., pieces of a larger thrombus within the blood vessel) by increasing a size of the proximal mouth 20 through which the thrombi may enter the basket 22. In some examples, a maximum cross-sectional dimension (e.g., a maximum diameter) of the proximal mouth 20 may be roughly the same point as the maximum cross-sectional dimension $D_1$ of the expandable element 14.

The maximum cross-sectional dimension $D_1$ of the expandable element 14 in its deployed state, when unconstrained by a catheter lumen, a body lumen, or the like, may be selected based on the body lumen in which the thrombus removal device 10 is intended to be used. For example, the maximum outer cross-sectional dimension $D_1$ of the expandable element 14 may be selected to be oversized relative to the body lumen, e.g., by 5% to 25%, such as about 10%, in order to enable the expandable element proximal end 14A to be in apposition to the wall of the body lumen when the device 10 is deployed in the body lumen. The apposition between the proximal end 14A (including the proximal mouth 20) and a blood vessel wall may help the thrombus removal device 10 collect a larger percentage of the thrombus. In some examples, the maximum cross-sectional dimension $D_1$ is 20 mm, while the maximum cross-sectional dimension $D_2$ at the distal end 14B of the expandable element 14 is 2 mm. The example dimensions described herein for the thrombus removal device 10 are not exhaustive. An expandable element 14 having any suitable diameter may be employed and may be sized for deployment into the vasculature of any suitable subject.

The expandable element 14 may have any suitable length, which can be measured from the proximal end 14A to the distal end 14B along a central longitudinal axis 28 of the expandable element support structure 12. In some examples, the expandable element 14 has a length of about 50 mm to about 150 mm. In some examples, the length is selected to facilitate a particular anatomical location. For example, the expandable element 14 can have a length that enables the proximal end 14A of the expandable element 14 to be positioned at the base of the interior vena cava while keeping the distal end 14B out of the right atrium. For example, the expandable element 14 can have a length of less than or equal to about 150 mm.

The expandable element support structure 12 is positioned generally along the longitudinal axis 28, which extends from the proximal end 14A of the expandable element 14 to the distal end 14B of the expandable element 14.

The expandable element 14 defines a plurality of openings 24 of uniform or various nonuniform dimensions. For example, the expandable element 14 may be formed from a mesh or braided structure, or a cut (e.g., a laser-cut) tube. The plurality of openings 24 may be formed by mechanical means such as laser cut, drilling, and punching, by chemical means such as the selective dissolution of one or more components, or by virtue of a braided structure. Other examples of suitable materials for the expandable element 14 may also include braided, knitted, woven, or non-woven fabrics that are capable of retaining particulate debris while permitting fluid to flow through the expandable element 14. Other suitable configurations for the expandable element 14 include a laser-cut frame, such as a laser-cut nitinol frame.

In some cases, the expandable element 14 may be used multiple times for the same patient (e.g., for multiple passes of the same thrombus or different passes of different thrombus), and cleaned between passes. A laser-cut frame may include fewer crossing points than a braided expandable element, which may make cleaning the expandable element 14 to remove any captured thrombus easier. Crossing points between filaments of a braid or other structure may trap parts of the thrombus and, thus, make cleaning of the expandable element 14 more difficult and time consuming. Further, a braid may be more likely to elongate and decrease in diameter during cleaning compared to a laser cut tube (e.g., as the expandable element 14 is rinsed in saline or wiped to remove thrombus fragments). The decrease in the diameter of a braided expandable element may also make removing the thrombus fragments from the expandable element 14 during cleaning more difficult compared to a laser-cut tube.

In some examples, the expandable element 14 has a configuration that facilitates the withdrawal of the expandable element 14 into a sheath, e.g., to remove the expandable element 14 from the vasculature or to reposition the expandable element 14 within the vasculature. For example, the expandable element 14 may be formed to be seamless (e.g., laser cut tube) and have closed cells. Seams or parts of an expandable element defining an open cell may catch on the distal end of a sheath during the resheathing process. Thus, eliminating seams and/or open cells may help facilitate easier resheathing of the expandable element.

The plurality of openings 24 have an average maximum cross-sectional dimension that enables the expandable element 14 to retain pieces of a thrombus, while enabling fluid (e.g., blood) to flow through the openings 24. In some examples, the plurality of openings 24 have an average maximum cross-sectional dimension of 1 mm to about 10 mm. The size of the openings 24 can depend on the vessel diameter to which the device 10 is apposed. In some examples, when the device 10 is configured to be expanded in apposition to a vessel having a 16 mm diameter, the openings 24 have an average maximum cross-sectional dimension of about 4 mm to about 8 mm. When the expandable element 14 is in the expanded or deployed configuration, the maximum cross-sectional dimension being measured across the respective opening around the circumference (or other outer perimeter in the case of non-circular expandable elements 14) of the expandable element 14 at a given cross section of the overall device 10.

In some examples, the shapes of the openings 24 may dynamically change depending on a combination of any pressure applied from any foreign substance, such as a thrombus or other occlusive matter, and a material composition of the expandable element 14. For example, as the expandable element 14 is in the delivery configuration moving distally through a thrombus, the cross-sectional openings may be at a minimum dimension and, as the expandable element 14 is in the deployed configuration moving proximally through the thrombus, the openings 24 may increase in size.

The basket 22 of the expandable element 14 defines an interior cavity 26 configured to receive and retain pieces of a thrombus via the proximal mouth 20. The plurality of openings 24 is present in the portion of the expandable element 14 defining the basket 22. Thus, when the expandable element 14 is in its deployed configuration within a blood vessel lumen, fluid (e.g., blood) can flow through the expandable element 14 past portions of the thrombus captured inside the interior cavity 26 of the basket 22. In some examples, the sizes of the openings 24 are constant throughout the basket 22, while in other examples, the average size of the openings 24 varies throughout the basket 22. For example, the average size of the openings 24 may decrease from the proximal end 14A to the distal end 14B of the basket 22 to help prevent the escape of collected thrombus portions from the basket 22 during retrieval of the thrombus removal device 10 from a patient.

In the deployed configuration of the thrombus removal device 10, an outer surface of the expandable element 14 tapers in a distal direction along a majority of the length of the basket 22. For example, the expandable element 14 can taper in a distal direction along a majority of the length of the basket 22. This taper may define a conical shape of the basket 22, as shown in FIG. 1.

In some examples, the expandable element 14 tapers from a diameter of about 20 mm at the proximal end 14A to a diameter of about 2 mm at the distal end 14B. In some examples, the expandable element 14 may define a constant taper in the distal direction, as shown in FIG. 1. In other examples, the expandable element 14 defines a stepped taper or a gradual taper in the distal direction. The stepped taper may be achieved using any combination of geometries, such as, but not limited to, a proximal cylindrical segment followed by a proximal frustoconical segment, which can, in some cases, be followed by a distal cylindrical segment and a distal frustoconical segment. The gradual taper may be achieved using any combination of geometries, such as, but not limited to, a proximal frustoconical segment, followed by one or more additional frustoconical segments, at least two of the frustoconical segments having different degrees of taper. The taper segments (e.g., the frustoconical segments) may be any angle (e.g., 10 degrees to 80 degrees) relative to a longitudinal axis of the expandable element support structure 12.

As a result of the tapering configuration, only a relatively small length of the expandable element 14 is configured to contact an inner wall of the blood vessel when the expandable element 14 is deployed within the blood vessel. This may enable the expandable element 14 to both achieve some apposition with the blood vessel wall to capture more thrombus material, while reducing the adverse interaction between the expandable element 14 and the wall of the blood vessel as a clinician pulls the expandable element 14 proximally through the blood vessel 34 and through the thrombus 36. Overly contacting the vessel wall may lead to vessel spasms and adverse effects to the inner layer of the vessel, which may lead to further thrombosis. In some examples, the length of the contact between the expandable element 14 and the vessel wall when the thrombus removal device 10 is deployed in the vessel is about 5 mm to about 50 mm, such as about 5 mm, 10 mm, or 50 mm. The length of the contact between the expandable element 14 and the wall of vessel 34 may increase with smaller-diameter vessels as the largest diameter (or other cross-sectional dimension) of the basket 22 will be compressed.

In some examples, the proximal end 14A (e.g., an outer perimeter of the proximal mouth 20) is configured to have an outward radial force greater than the radial force of the basket 22 of the expandable element 14 to help ensure apposition to the vessel wall. The basket 22 may be configured to exert less radial force, even if it contacts the vessel wall. The greater radial force may not only help ensure greater apposition with a vessel wall, but may also facilitate disruption of a thrombus. The greater radial force may be achieved using any suitable technique, such as, but not limited to, including a proximal ring that is configured to expand radially outward, e.g., in response to being released from an inner lumen of a delivery catheter.

A thrombus may not be uniformly distributed within a blood vessel. Rather than relying on a clinician to guide the expandable element 14 to the side of the vessel wall that has the largest volume of the thrombus, the apposition of the circumference of the proximal mouth 20 and the blood vessel wall may help center the expandable element 14 in the vessel to capture a larger volume of thrombus. In some examples, the expandable element 14 is configured to self-center in the vessel due at least in part to the proximal portion of the expandable element 14 being configured to stay in apposition with the vessel wall and/or being radially symmetric about longitudinal axis 28. This may enable the expandable element 14 to stay open and conform to vessel curvature when used with many clot types (e.g., which may have different densities) improving wall to wall contact.

Further, having only a relatively small length of the expandable element 14 configured to contact an inner wall of the blood vessel may enable the expandable element 14 to product less drag force (i.e., less force needed to be exerted by the clinician) to move the device 10 through the vessel.

In some examples, a proximal part of the expandable element 14, e.g., the proximal mouth 20, which may correspond to about the first 5 mm to about 20 mm of the expandable element 14, is configured to have more radial force to help ensure apposition to the vessel wall when the expandable element 14 is in the deployed configuration in the blood vessel. In some of these examples, the remaining distal length of the expandable element 14 is configured to exert less radial force than the proximal part to enable the remaining distal length pass more passively through the vessel 34.

At least in part due to the tapered configuration of the expandable element 14 and the corresponding decrease in volume of the basket 22, the expandable element 14 is configured to compress at least a part of the thrombus received within the basket 22 as the expandable element 14 is proximally withdrawn into a catheter. A thrombus may have a relatively large liquid content. Thus, by compressing the thrombus, fluid may be expelled from the thrombus and dehydrate the thrombus, such that the volume of the thrombus retained in the basket 22 is decreased. Decreasing the volume of the thrombus in the basket 22 may help increase the ease with which the expandable element 14 may be withdrawn proximally into the inner lumen of a catheter to withdraw the thrombus from the patient.

The tapered shape of the expandable element 14 may help distribute the thrombus longitudinally within the basket 22 as the expandable element 14 is proximally withdrawn into a catheter, which may help mitigate the possibility of having too much relatively rigid material (e.g., the dehydrated thrombus) at the distal-most end 14B of the basket 22. A relatively large bulk of relatively rigid material at the distal-most end of the basket 22 may interfere with the proximal withdrawal of the expandable element 14 into a retrieval catheter. For example, while moving the expandable element 14 proximally through the thrombus, the thrombus may be captured within the basket 22 and then compressed within the expandable element 14 as the thrombus is forced toward the distal end 14B of the expandable element 14. As noted above, this compression may expel liquid within the thrombus as the expandable element 14 elongates while the expandable element support structure 12 moves proximally through a blood vessel 34.

The distribution of the thrombus longitudinally within the basket 22, as well as the compression of the thrombus within the basket 22 may help the expandable element 14 retain and remove a relatively large thrombus from a blood vessel of a patient for a given size of the expandable element 14.

The thrombus removal device 10 includes a stationary element 18 and a movable element 38. The movable element 38 is configured to move relative to the stationary element 18. The stationary element 18 includes a plurality of elongated arms 18A-18N. In the example shown in FIG. 1, each of the arms 18A-18N has proximal and distal ends extending from (e.g., mechanically coupled to) the expandable element support structure 12. Thus, the proximal and distal ends of the stationary element 18 are configured to have fixed longitudinal and rotational positions relative to the expandable element support structure 12.

At least a central portion of each of the arms 18A-18N is configured to extend radially outward, away from the expandable element support structure 12, into an expanded or deployed configuration in order to segment a thrombus 36 (FIG. 2) into a plurality of pieces (e.g., two or more smaller thrombus portions) as the stationary element 18 is moved proximally through the thrombus 36. In some examples and with some patient anatomies, while the stationary element 18 is in a deployed configuration, the central portions of arms 18A-18N may be configured to, as a group, span across the entire area of occlusion of the proximal mouth 20 of the expandable element 14 to well under 10% of the cross-sectional area of the proximal mouth 20 (the cross-section being taken in a direction orthogonal to the longitudinal axis 28), enabling the arms 18A-18N to segment the thrombus 36 with minimal force without impeding the thrombus pieces from entering the mouth 20. In some examples, the stationary element 18 includes three elongated arms, each having a cross-sectional width (the cross-section being taken in a direction orthogonal to longitudinal axis 28) of about 0.25 mm. Minimizing the area of contact between the thrombus 36 and the stationary arms 18A-18N may facilitate the shearing process of the stationary arms 18A-18N as they pass through and segment the thrombus 36.

The stationary arms 18A-18N may have any suitable radial spacing, e.g., be evenly distributed around the central longitudinal axis 28 (e.g., for three stationary arms 18A-18N, the stationary arms may be 120 degrees apart from each other) or may be unevenly distributed around the central longitudinal axis 28. In examples in which the stationary element 18 extends at least partially through the proximal mouth 20 of the basket 22, the number of stationary arms 18A-18N and the radial spacing between the stationary arms 18A-18N may be selected to enable the proximal mouth 20 of the expandable element 14 to remain relatively open, centered around the expandable element support structure 12, and to enable pieces of the thrombus 36 to move distally into the basket 22 rather than being captured and retained within the spaces between the stationary arms 18A-18N. In addition, the number of the stationary arms 18A-18N may be selected to enable the thrombus 36 to be segmented into sufficiently small pieces (FIG. 2) for collection in the basket 22 after moving distally through the proximal mouth 20.

In some examples, but not all examples, some or all of the plurality of stationary arms of stationary element 18 may be integrally formed with the expandable element 14. For example, some or all of the stationary arms 18A-18N and the expandable element 14 may be formed from a common piece of material (e.g., a nitinol tube). In other examples, some or all of the stationary arms 18A-18N may be formed separately from the expandable element 14 and remain separate or may be subsequently connected to expandable element. For example, some or all of the stationary arms 18A-18N may be formed separate from the expandable element 14 and may be connected to a point at or near the circumference of the proximal mouth 20 of the expandable element 14 using any suitable technique, such as, but not limited to, adhesives, solder, welding, crimped elements, such as bands or beads, and other suitable fixation mechanisms and/or elements. As one example, a central portion of some or all of the stationary arms 18A-18N may be coupled to a rim or circumference of proximal mouth 20 of expandable member 14. As another example, a distal end of some or all of the stationary arms 18A-18N may be coupled to a rim or circumference of proximal mouth 20 of expandable member 14. In these examples, the plurality of stationary arms 18A-18N may be formed from the same material or substantially the same material as the expandable element 14.

In addition, the stationary arms of stationary element 18 may be formed separate from or may be integrally formed with the expandable element support structure 12. In examples in which the plurality of stationary arms 18A-18N are formed separate from the expandable element support structure 12, the proximal and/or distal ends of each stationary arm 18A-18N may be connected to the expandable element support structure 12 using any suitable technique, such as by an adhesive, solder, welding, crimped elements, such as bands or beads, and other suitable fixation mechanisms and/or elements.

The arms 18A-18N of the stationary element 18 are configured to remain rotationally and/or longitudinally stationary relative to a part of the expandable element 14 (e.g., the proximal mouth 20) and/or the expandable element support structure 12. The movable element 38 is configured to move relative to the stationary element 18 and macerate the thrombus 36 after the stationary element 18 segments the thrombus 36 into smaller pieces (relative to the state before the use of thrombus removal device 10). Thus, the stationary element 18 is configured to segment the thrombus 36 into smaller pieces and the movable element 38 is configured to break the smaller pieces into even smaller pieces.

The movable element 38 is located radially inward from the stationary element 18, e.g., closer to the central longitudinal axis 28 of the expandable element support structure 12 than the stationary element 18. As shown in FIG. 1, the movable element 38 is positioned within a volume 80 defined by the stationary arms 18A-18N of the stationary element 18. Thus, the movable element 38 has a greatest cross-sectional dimension (e.g., a diameter) that is smaller than a greatest cross-sectional dimension of the movable element 18, the cross-sections being taken in a direction orthogonal to the longitudinal axis 28 when the elements 18, 38 are in an expanded (deployed) configuration. In some examples, the movable element 38 has a greatest cross-sectional dimension (e.g., a diameter) that is smaller than a greatest cross-sectional dimension of the movable element 18 when the elements 18, 38 are in a collapsed (delivery) configuration. For example, the stationary arms 18A-18N may be configured to be positioned between the movable element 38 and the wall of the blood vessel 34 to protect the wall of the vessel 34 from the movable element 38, while still enabling the thrombus 36 to move into the volume 80 between adjacent stationary arms 18A-18N to contact the movable element 38.

The movable element 38 may take the form of any suitable configuration and be configured to (e.g., be controllable to) move relative to the stationary element 18 according to any suitable motion pattern in order to more-thoroughly break down the thrombus 36. FIG. 1 depicts a first non-limiting example of the movable element 38. In the example depicted in FIG. 1, the movable element 38 includes a second plurality of elongated arms 38A-38N (e.g., "movable arms 38A-38N") having distal ends extending from (e.g., slidably or mechanically coupled to) the expandable element support structure 12. A proximal end of each of the movable arms 38A-38N may be connected to an elongated movable element support structure 60 that is configured to transfer a movement (e.g., rotation, vibration, and/or plunging movement) to the movable element 38 from an actuator device 66 at a proximal portion of the thrombus removal device 10.

The actuator device 66 can include any suitable motor and control circuitry configured to generate movement and transfer the motion to movable element 38 via movable element support structure 60. The actuator device 66 may also include, for example, a user-input mechanism communicatively coupled to the control circuitry. The control circuitry, as well as other processors, processing circuitry, controllers, control circuitry, and the like, described herein, may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, control circuitry 42 may include multiple components, such as any combination of one or more microprocessors, one or more DSPs, one or more ASICs, or one or more FPGAs, as well as other discrete or integrated logic circuitry, and/or analog circuitry.

The movable element support structure 60 can be, for example, a tube that is positioned radially outward of the expandable element support structure 12 to which the expandable element 14 is connected. The movable element support structure 60 is configured to move independently of the expandable element support structure 12.

A distal end of each of the movable arms 38A-38N may be connected to a distal movable element support structure 92, which is configured to move with the movable element 38 (e.g., rotate about the central longitudinal axis 28, vibrate, and/or move longitudinally along the central longitudinal axis 28) and move relative to stationary element 18. The distal movable element support structure 92 can be, for example, a tubular or ring-like structure that fits around the expandable element support structure 12 and is configured to rotate about the central longitudinal axis 28 relative to the expandable element support structure 12 as the movable element 38 similarly rotates and/or move longitudinally relative to the stationary arms 18A-18N along a direction parallel to the central longitudinal axis 28 as the movable element 38 similarly moves longitudinally.

While in a deployed configuration, a central portion of each of the movable arms 38A-38N is configured to spread radially outward from the expandable element support structure 12 in order to macerate the thrombus 36 (FIG. 2) into a plurality of pieces (e.g., two or more smaller pieces) while the movable arms 38A-38N move relative to the stationary element 18. For example, the movable arms 38A-38N of movable element 38 may be configured, according to various non-limiting examples, to rotate about the longitudinal axis 28 and relative to the stationary element 18, to oscillate parallel to the longitudinal axis 28 and relative to the stationary element 18 (while remaining within the volume 80 defined by the stationary element 18), to vibrate radially inward and outward from the longitudinal axis 28 and relative to the stationary element 18, and/or to plunge proximally and distally along longitudinal axis 28 and relative to the stationary element 18 in order to macerate the thrombus 36.

Figure 2:
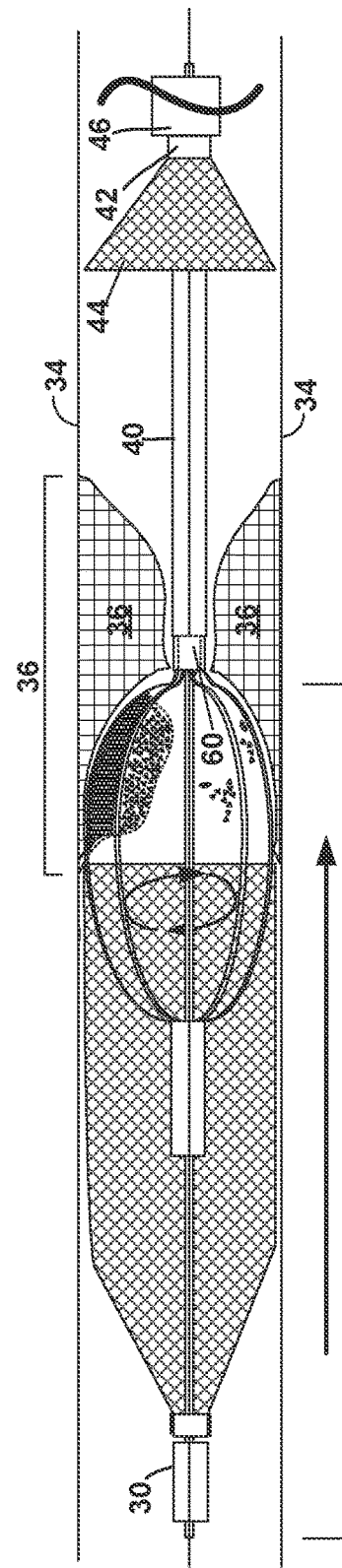
FIG. 2 is a conceptual illustration of a thrombus being separated into smaller pieces by the thrombus removal device of FIG. 1.

FIG. 2 is a conceptual illustration of the example stationary element 18 and the example movable element 38 of FIG. 1 while segmenting and macerating an example thrombus 36 into a plurality of smaller pieces. More specifically, FIG. 2 is a conceptual side elevation view of the expandable element 14, the stationary element 18, and the movable element 38 moving proximally (to the right, from the perspective shown in FIG. 2) through the thrombus 36 and illustrates the thrombus pieces after they have been separated from a larger thrombus portion and as they are entering the basket 22 of the expandable element 14.

In the example of FIG. 2, stationary element 18 and movable element 38 are fully expanded into a deployed configuration (as compared to a partially expanded configuration as shown in FIG. 1), such that a diameter of the stationary element 18 extends approximately the full width of a vessel 34 of a patient into which the thrombus removal device 10 has been inserted. In the deployed configuration, the stationary element 18 may define a diameter (transverse to longitudinal axis 28) that is less than, approximately equal to, or greater than the diameter of proximal mouth 20 of the expandable element 14. In the example shown in FIG. 2, the diameter of stationary element 18 and proximal mouth 20 are both approximately equal to the width of the vessel 34 while in their respective deployed configurations.

Also shown in FIG. 2 is a delivery catheter 40, a retrieval catheter 42 defining or otherwise including a funnel 44, and a cover sheath 46. The entire length of the catheters 40, 42, and the cover sheath 46 is not shown in the figures. For example, the retrieval catheter 42 shown in FIG. 2 is shown to be relatively short, but may in use have a length long enough to extend from a target site within a patient to a location outside of the patient.

Separating the thrombus 36 into a plurality of smaller thrombus portions may enable more-effective capture of the thrombus 36 within the basket 22, particularly when the thrombus 36 may be a sub-acute thrombus that is more organized and/or vessel-wall-adherent compared to a more-newly formed acute thrombus, which may be softer. In addition, separating the thrombus 36 into a plurality of smaller thrombus portions may enable a smaller delivery and/or retrieval catheter to be used to deliver or withdraw, respectively, the thrombus removal device 10 from the patient.

Once the thrombus removal device 10 is in a position distal to a thrombus 36, and deployed from the delivery catheter 40, a clinician may move the expandable element support structure 12, and as a result, the fixedly connected stationary element 18, and the movable element 38 (in their respective deployed configurations) proximally through the thrombus. As shown in FIG. 2, while moving the stationary element 18 and the expandable element 14 proximally through the thrombus 36, the elongated stationary arms 18A-18N of stationary element 18 will come in contact with a distal portion of the thrombus 36 and segment the thrombus 36 into smaller pieces (e.g., will cleave one or more sections from the larger occlusive mass). Similarly, the movable element 38 will come into contact with a distal portion of the thrombus 36, and through a pre-defined motion (e.g., a rotational motion, as depicted in the example of FIG. 2), the movable element 38 will macerate the distal portion of the thrombus 36 into even smaller portions, at least some of which are then received in the proximal mouth 20 of the expandable element 14. As the proximal mouth 20 receives the macerated thrombus portions, the macerated thrombus portions will move distally within the expandable element 14 through the basket 22, where the thrombus portions may be retained.

In some examples, one or more disassociated segments of the thrombus 36 may become entangled within the one or more of the openings 24 defined by the expandable element 14. For example, as the part of the thrombus 36 within the basket 22 becomes compressed, some of the thrombus may be squeezed out one or more of the openings 24. However, even these parts of the thrombus 36 extending through the one or more openings 24 may still be considered captured within the basket 22. For example, the more rigid dehydrated thrombus extending through the opening 24 may be less likely to separate from the expandable element 14 and flow downstream.

In some examples, the thrombus removal device 10 can include an atraumatic distal tip that is configured to soften an interface between the distal tip and adjacent tissue of a patient. For example, as shown in FIGS. 1 and 2, the thrombus removal device 10 can include a distal tip member 30 at or near a distal end of the expandable element support structure 12. The distal tip member 30 can be formed from any suitable material, such as, but not limited to, a relatively soft polymer that is softer than the material forming the expandable element support structure 12. In some examples, the distal tip member 30 may also act as the distal slider 32, which is configured to movably connect the distal end 14B of the expandable element 14 to the expandable element support structure 12 and is configured to slide relative to the expandable element support structure 12.

The configuration (e.g., shape, dimensions, and the like) and the composition (e.g., material) of the thrombus removal device 10, including the expandable element support structure 12, the expandable element 14, the stationary element 18, and the movable element 38, of the examples described herein are merely one example. In other examples, for example, the expandable element 14, the expandable element support structure 12, the stationary element 18, and/or the movable element 38 may have another configuration.

Figure 3:
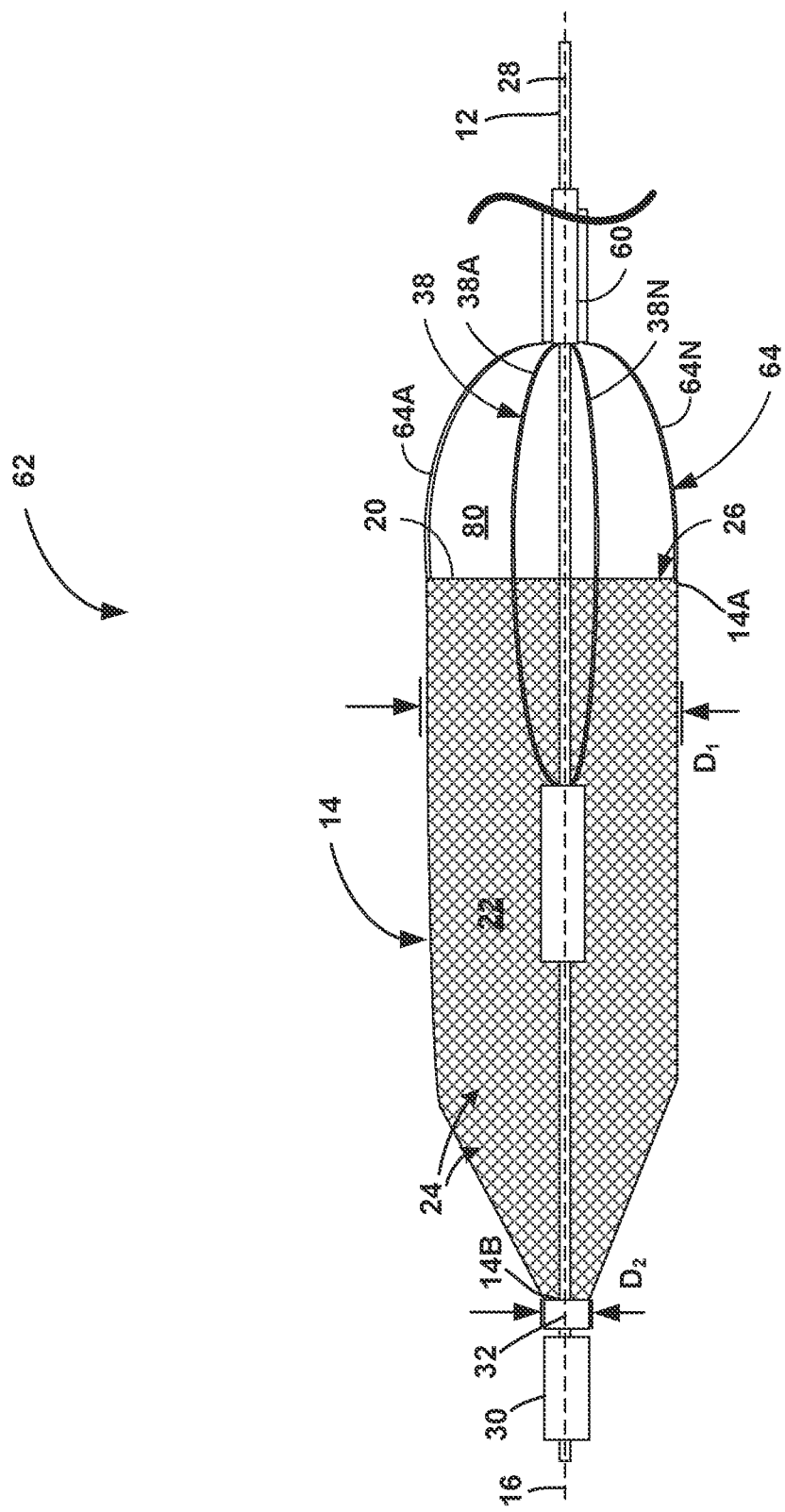
FIG. 3 is a conceptual side elevation view of another example thrombus removal device.

In the example shown in FIG. 1, each of the arms 18A-18N of the stationary element 18 has proximal and distal ends extending from (e.g., mechanically coupled to) the expandable element support structure 12. In other examples, however, some or all of the arms 18A-18N may be connected to another structure of the thrombus removal device 10. For example, FIG. 3 is a conceptual side elevation view of another example thrombus removal device 62. The thrombus removal device 62 is similar to the thrombus removal device 10 of FIGS. 1 and 2, but unlike the thrombus removal device 10, the thrombus removal device 62 includes a stationary element 64 including elongated stationary arms 64A-64N that are mechanically coupled to the expandable element support structure 12 at a proximal end of the respective stationary arm 64A-64N and are coupled to the rim of proximal mouth 20 of expandable element 14 at a distal end of the respective stationary arm 64A-64N. In contrast, the stationary arms 18A-18N of the thrombus removal device 10 of FIGS. 1 and 2 are mechanically coupled to the expandable element support structure 12 at both proximal and distal ends. In the configuration shown in FIG. 3, the stationary element 64 and the expandable element 14 may be mechanically integrated, such that stationary element 64 and expandable element 14 are configured to convert between a delivery configuration and a deployed or expanded configuration in concert with one another.

Figure 4:
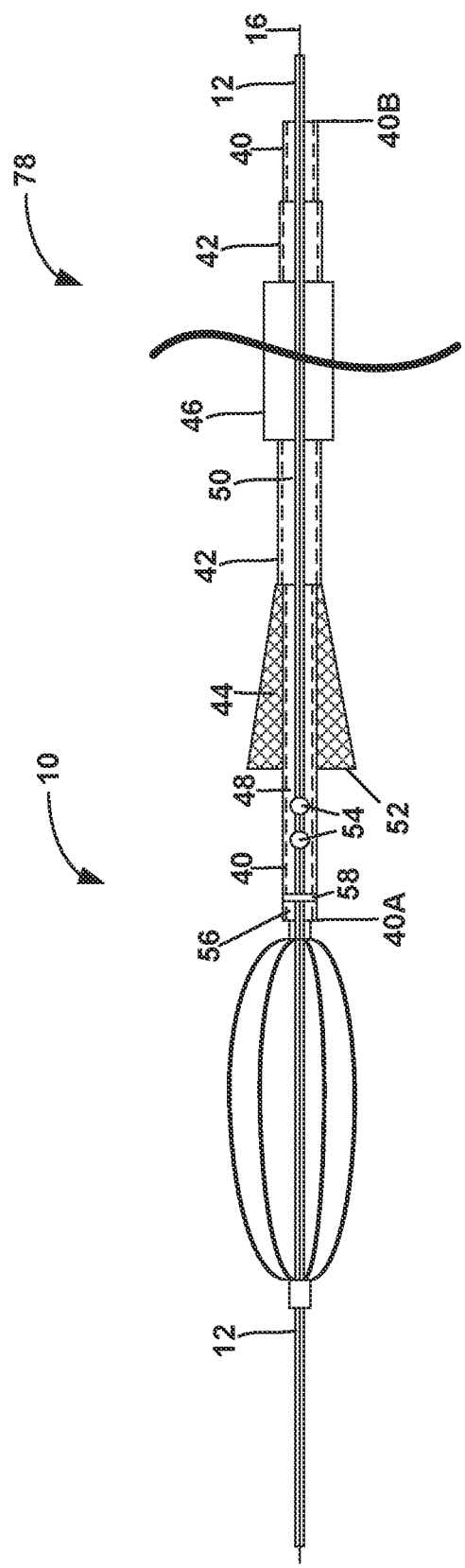
FIG. 4 is a conceptual side elevation view of an example thrombus removal device, where an expandable element has been removed from the figure to show details of a stationary element and a movable element.

FIG. 4 is a conceptual side elevation view of the example thrombus removal device 10 of FIGS. 1 and 2 and a catheter assembly 78, where the expandable element 14 has been removed from the figure to show details of the stationary element 18 and the movable element 38. Although FIG. 4 is described with reference to the thrombus removal device 10 of FIGS. 1 and 2, in other examples, the catheter assemblies and techniques described herein can be used with the other example the thrombus removal devices described herein, including the thrombus removal device 62 of FIG. 4. The catheter assembly 78 includes the delivery catheter 40, the retrieval catheter 42 defining or otherwise including the funnel 44, and the cover sheath 46 configured to cover the funnel 44 and hold the funnel 44 in a low-profile configuration for delivery of the catheter assembly 78 to a target site. The entire length of the structures shown in FIG. 4 are not shown. For example, the retrieval catheter 42 is shown to be truncated in length. Although the delivery catheter 40, the retrieval catheter 42, and the cover sheath 46 are shown as being nested relative to each other in FIG. 4, in use, a clinician may deliver the thrombus removal device 10 to a target site within a patient over the guidewire 16 and while the device 10 is within a lumen 48 of the delivery catheter 40, and then, at a later time, introduce the retrieval catheter 42 and cover sheath 46 into the patient over the guidewire 16 or the delivery catheter 40 at a later time, e.g., after thrombus is collected in the basket 22 of the thrombus removal device 10. In other examples, however, the clinician may deliver the thrombus removal device 10 with the delivery catheter 40, the retrieval catheter 42, and the cover sheath 46 nested together.

The delivery catheter 40 and the retrieval catheter 42 have any suitable configuration. For example, each of the catheters 40, 42 may have a tubular catheter body that defines a respective lumen 48, 50. In some examples, one or both catheters 40, 42 may be a multi-lumen catheter that defines a plurality of lumens. In any of these examples, the catheters 40, 42 may be formed from any suitable material, such as, but not limited to, such as poly(tetrafluoroethylene) (PTFE), polyethylene (PE), high density polyethylene (HDPE), low density polyethylene (LDPE), other flexible plastic blends or thin-walled metal alloys or combinations thereof.

The delivery catheter lumen 48 is configured to contemporaneously receive the thrombus removal device 10, including the guidewire 16, the expandable element 14, the stationary element 18, and the movable element 38, as well as part of the expandable element support structure 12. When the thrombus removal device 10 is positioned within the delivery catheter lumen 48, the walls of the delivery catheter 40 apply a compressive force to the thrombus removal device 10 to hold the thrombus removal device 10 in a relatively low profile delivery configuration. In FIG. 4, the thrombus removal device 10 is shown in its deployed configuration, after it has been deployed from a distal end 40A of the delivery catheter 40. To deploy the thrombus removal device 10, a clinician may push the thrombus removal device 10 from the delivery catheter lumen 48 by applying a pushing force to a proximal portion of the expandable element support structure 12 proximally extending from a proximal end 40B of the delivery catheter 40. The expandable element support structure 12 is rigid enough to move distally out the delivery catheter distal end 40A in response to the pushing force. In addition to or instead of applying the pushing force to the expandable element support structure 12, the clinician may deploy the thrombus removal device 10 from the delivery catheter 40 by at least proximally withdrawing the delivery catheter 40 relative to the expandable element 14, e.g., while holding the thrombus removal device 10 in place or nearly in place via the expandable element support structure 12.

The retrieval catheter 42 is configured to receive the thrombus removal device 10 after thrombus is collected in the basket 22 of the expandable member 14 (FIGS. 1 and 2). The retrieval catheter lumen 50 is configured to contemporaneously receive the guidewire 16, the expandable element 14, the stationary element 18, and the movable element 38, as well as part of the expandable element support structure 12 and, in some examples, the delivery catheter 40. However, the delivery catheter 40 and/or the guidewire 16 may be removed from the patient prior to introducing the retrieval catheter 42 over the expandable element support structure 12 of the thrombus removal device 10.

The funnel 44 is positioned at a distal portion (e.g., a distal end) of the retrieval catheter 42 and is configured to facilitate the proximal withdrawal of the expanded thrombus removal device 10 into the retrieval catheter lumen 50. For example, the funnel 44 defines a relatively large distal funnel mouth 52 and the funnel 44 tapers in a proximal direction from the distal funnel mouth 52. The tapered shape of the funnel 44 guides the thrombus removal device 10 from the distal funnel mouth 52 into the retrieval catheter lumen 50, while compressing the thrombus removal device 10 from the deployed configuration to a smaller profile configuration, e.g., the delivery configuration or a retrieval configuration that is smaller in profile than the deployed configuration but may be larger in profile than the delivery configuration due to the presence of collected occlusive material within the basket 22 of the expandable element 14.

To help hold the funnel 44 in a lower profile configuration during the navigation of the retrieval catheter 42 through vasculature to the deployed thrombus removal device 10 within the body of the patient, the catheter assembly 78 may include a cover sheath 46 that is configured to apply a compressive force to the funnel 44. Once the cover sheath 46 is proximally withdrawn so that it no longer covers the funnel 44, the funnel 44 may expand radially outward into the funnel shape shown in FIG. 4. For example, the funnel 44 may have a self-expandable frame, e.g., formed from nitinol struts, a nitinol mesh, or a nitinol braid or another suitable material, that is shape set to the funnel shape. As another example, the funnel 44 may be expanded radially outward with the aid of an expansion mechanism, such as a balloon.

In some examples, the funnel 44 is configured to be re-introduced into the cover sheath 46 after it is deployed from the cover sheath 46, such as by withdrawing the funnel 44 proximally into the cover sheath 46, by moving the cover sheath 46 distally over the funnel 44, or any combination thereof. Resheathing the funnel 44 in this manner may facilitate removal of the funnel 44 from the vasculature of the patient or an adjustment of the position of the funnel 44 within the vasculature. The funnel 44 can have a configuration that facilitates resheathing. For example, the funnel 44 can have a closed cell braid pattern (e.g., no open strands at the proximal end) that is less likely to catch on the distal end of the cover sheath 46 than open cells as the funnel 44 is re-introduced into the cover sheath 46.

In some examples, the retrieval catheter 42 includes a plurality of pores configured to enable liquid to exit the retrieval catheter inner lumen 50 and into, e.g., the blood stream. For example, the pores may be positioned along the funnel 44 and/or along a sidewall of the catheter 42 proximal to the funnel 44. The liquid may be expelled from thrombus within the basket 22 as the expandable element 14 is proximally withdrawn into the funnel 44. The plurality of pores of the retrieval catheter 42 may have a size sufficient to permit fluid to flow out of the retrieval catheter inner lumen 50 and may have any suitable shape (e.g., oval, circular, square, rectangular, triangular, or an irregular shape). For example, the plurality of pores can be defined by a sidewall of the retrieval catheter 42 and having a greatest cross-sectional dimension (e.g., a diameter in the case of circular pores) of about 1 mm to about 10 mm, such as about 5 mm. Cross-sectional dimension as used herein may refer to a diameter, a width, or an average diameter $D_A$, with $D_A=4A/P$ where A is the area of the cross-section and P is the perimeter of the cross-section.

As shown in FIG. 4, the delivery catheter 40 may have a smaller profile (e.g., outer diameter or other maximum outer cross-sectional dimension) than the retrieval catheter 42. This may be due at least in part to needing to accommodate the expandable element 14 after pieces of a thrombus are positioned within the basket 22, thereby increasing an overall profile of the expandable element 14.

In some examples, the clinician may leave the delivery catheter 40 in the blood vessel 34 (FIG. 2) during retrieval of the thrombus 36 and may deliver a therapeutic agent, e.g., a lytic agent, through the delivery catheter lumen 48 to the target site. For example, the therapeutic agent may be introduced into the delivery catheter lumen 48 at a proximal portion of the catheter 40 and delivered to the target site via an opening at a distal-most end of the delivery catheter 40, through one or more side openings 54 defined by a sidewall of the delivery catheter 40 (e.g., distributed along a wall of the delivery catheter 40 extending along a length of the expandable element support structure 12 or a part of the delivery catheter 40), or any combination thereof. In some examples, the sidewall 56 of the delivery catheter 40 defines a plurality of side openings 54 that are distributed (evenly or unevenly) along only a portion of the delivery catheter sidewall 56 that is proximal to the expandable element 14 when the expandable element 14 is disposed in the delivery catheter lumen 48. In other examples, however, the side openings 54 can also be defined in the portion of the sidewall 56 that longitudinally aligns with the expandable element 14 when the expandable element 14 is disposed in the delivery catheter lumen 48 and/or the portion of the sidewall that is distal to the expandable element 14.

Although side openings 54 on one longitudinal side of the sidewall 56 are shown in FIG. 4, in some examples, the side openings 54 may be disposed on the other longitudinal side of the sidewall 56, too (e.g., distributed around an outer circumference of the delivery catheter 40 in examples in which the delivery catheter 40 is circular in cross-section).

In some examples, the therapeutic agent is delivered via the delivery catheter lumen 48 after deploying the thrombus removal device 10, i.e., while the thrombus removal device 10 is no longer in the delivery catheter lumen 48. In addition to, or instead of, delivering the therapeutic agent after deploying the thrombus removal device 10, the therapeutic agent is delivered via the delivery catheter lumen 48 prior to deploying the thrombus removal device 10, for example, while the thrombus removal device 10 is still in the delivery catheter lumen 48. In some of these examples, the delivery catheter 40 can include a seal 58 positioned distal to the side openings 54 and proximal to the thrombus removal device 10 to help prevent the therapeutic agent from being delivered out a distal-most opening of the delivery catheter 40. The seal 58 may create a fluid-tight barrier that helps prevent the therapeutic agent from passing distally past the seal 58 towards the thrombus removal device 10. In other examples, however, the delivery catheter 40 may not include a seal 58 and instead the therapeutic agent may be free to be delivered out the distal-most opening of the delivery catheter 40 in addition to out of the side openings 54.

In other examples, the therapeutic agent is delivered via the delivery catheter lumen 48 after deploying the thrombus removal device 10, e.g., while the thrombus removal device 10 is no longer in the delivery catheter lumen 48.

Figure 5:
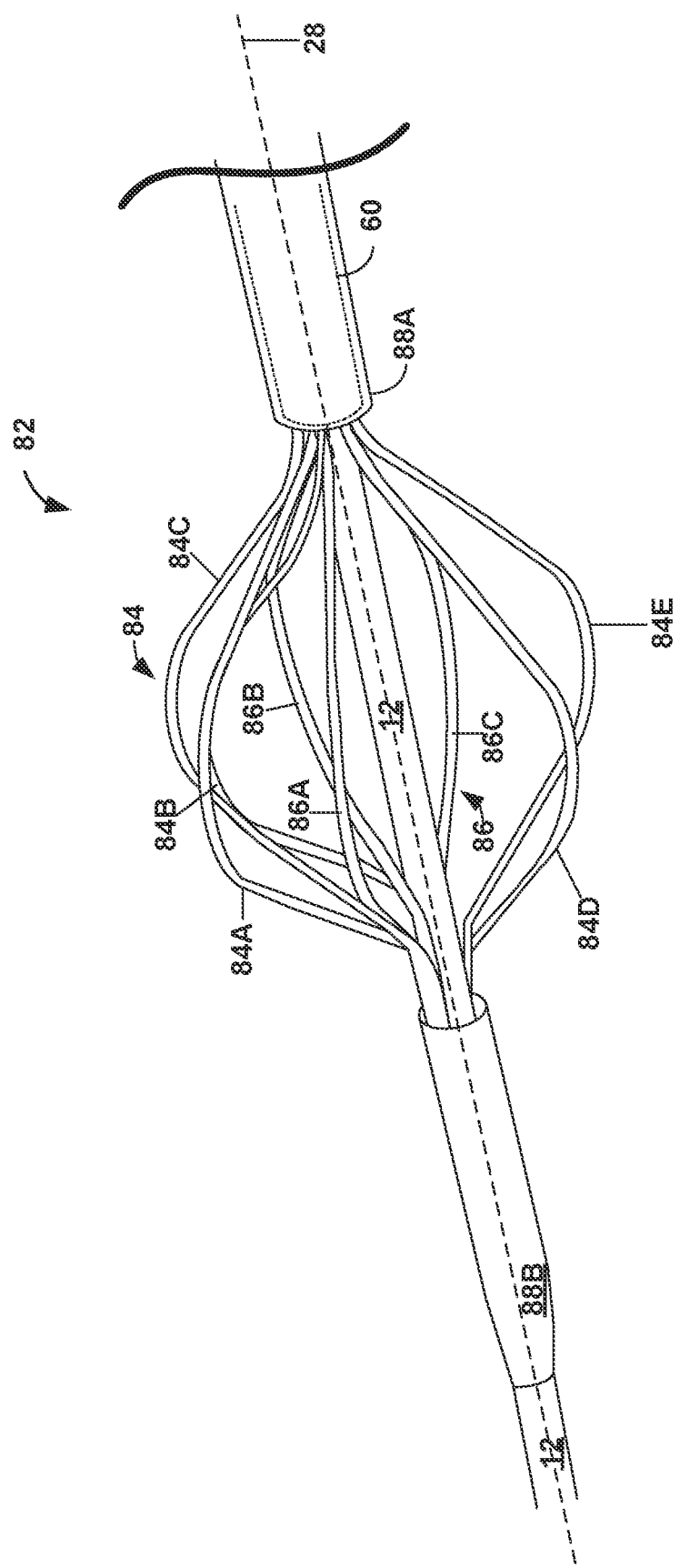
FIG. 5 is a perspective view of a portion of an example thrombus removal device.

FIG. 5 is a perspective view of a portion of an example thrombus removal device 82. The thrombus removal device 82 is an example of the thrombus removal device 10 of FIGS. 1 and 2. The thrombus removal device 82 includes the expandable element support structure 12, a stationary element 84, a movable element 86, a proximal end cap 88A, and a distal end cap 88B. As shown in FIG. 5, the stationary element 84 includes five elongated stationary arms 84A-84E, however, the stationary element 84 may include any number of stationary arms in other examples. The proximal and distal ends of the stationary arms 84A-84E are connected to the expandable element support structure 12. The stationary arms 84A-84E extend generally in a proximal-to-distal direction. In some examples, the proximal and distal ends of each respective stationary arm 84A-84E are aligned in a direction parallel to the longitudinal axis 28, such that the stationary arms are parallel to the longitudinal axis 28. In other examples, the one or more of the stationary arms 84A-84E may have misaligned proximal and distal ends such that respective stationary arms wrap circumferentially around an outer perimeter of the expandable element support structure 12 (e.g., defining part of a helix). In the deployed configuration shown in FIG. 5, a central portion of each of the stationary arms 84A-84E is configured to slice longitudinally through a thrombus 36 (FIG. 2) as the thrombus 36 passes through the stationary element 84, or as the stationary element 84 passes through the thrombus 36.

In the example shown in FIG. 5, the movable element 86 includes three elongated movable arms 86A-86C. The movable element 86 may include any number of movable arms, or in other examples, configurations other than, or additional to, elongated arms. As shown in FIG. 5, the movable arms 86A-86C may extend in a generally proximal-to-distal direction, and also generally wrap circumferentially around the central longitudinal axis 28, e.g., in a helical-type configuration. That is, in the example shown in FIG. 5, the proximal and distal ends of each movable arm 86A-86C are not aligned in a direction parallel to the longitudinal axis 28, such that the movable arms are not parallel to the longitudinal axis 28. In other examples, however, proximal and distal ends of some or all of the movable arms 86A-86C may be aligned in a direction parallel to the longitudinal axis 28.

Figure 6:
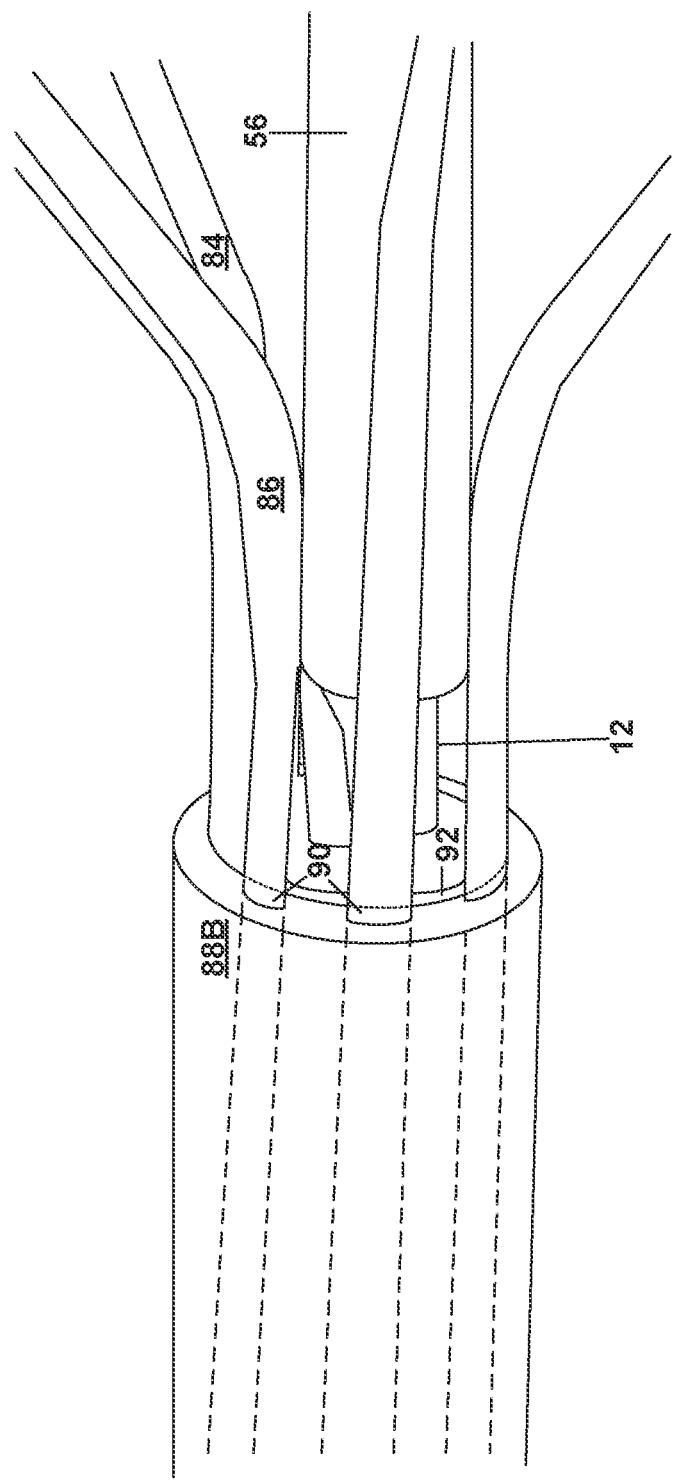
FIG. 6 is a close-up view of a distal portion of the example thrombus removal device of FIG. 5.

In some examples, a proximal end of the stationary element 84 is mechanically coupled to a proximal end cap 88A disposed on the expandable element support structure 12. Similarly, and as shown further in the close-up view of FIG. 6, in some examples, a distal end of the stationary element 84 and/or of the movable element 86 may be mechanically coupled to a distal end cap 88B disposed on the expandable element support structure 12. For example, as shown in FIG. 6, the distal end cap 88B may include a plurality of slots configured to rigidly retain distal portions of the stationary arms 84A-84E. Further, in some examples, the distal end cap 88B includes a ring structure 92, such as a rotatable tube configured to rigidly retain distal portions of the movable arms 86A-86C, enabling the movable element 86 to rotate about the expandable element support structure 12 and relative to the stationary element 84.

The movable element 86 is configured to move relative to the stationary element 84, and move within a volume defined by the stationary element 84, in order to macerate a thrombus 36 (FIG. 2) as the movable element 86 passes through the thrombus 36 (or as the thrombus 36 passes through the movable element 86). The movable element 86 is configured to move according to a predetermined motion pattern in order to macerate the thrombus 36. That is, the thrombus removal device 82 may be mechanically coupled to one or more control elements, such as actuator 66 (FIG. 1) configured to cause the movable element 86 to move according to a pre-determined pattern. As shown in FIG. 5, a proximal end of each of the elongated arms of movable element 86 is coupled to an elongated movable element support structure 60, which is configured to transfer a motion from the actuator 66 or other control device to movable element 86.

As one non-limiting example, the actuator device 66 may include a motor configured to cause the movable arms 86A-86C to rotate about the longitudinal axis 28 and relative to the stationary element 84. For example, the movable arms 86A-86C may be configured to spin within the volume defined by the stationary element 84 under the control of the actuator 66. In addition to or instead of rotating about the longitudinal axis 28, the actuator 66 can be configured to cause the movable element 86 to "plunge" back-and-forth (proximally and distally) in a direction generally parallel to the longitudinal axis 28 and relative to the stationary element 84, e.g., oscillating between proximal and distal directions of motion. In another example, instead of or in addition to the rotation or plunging movement, the actuator 66 can be configured to cause the movable arms 86A-86C to vibrate radially inward and outward from the longitudinal axis 28 and relative to the stationary element 84. In some examples, the actuator 66 and the movable element 86 are configured to enable the movable element 86 to move relative to the stationary element 84 according to a pre-determined combination of any or all of these example motion patterns. For example, the movable arms 86A-86C may be configured to move according to an arc-shaped motion, e.g., vibrating radially inward and outward and simultaneously in a circumferential direction.

Figure 7A:
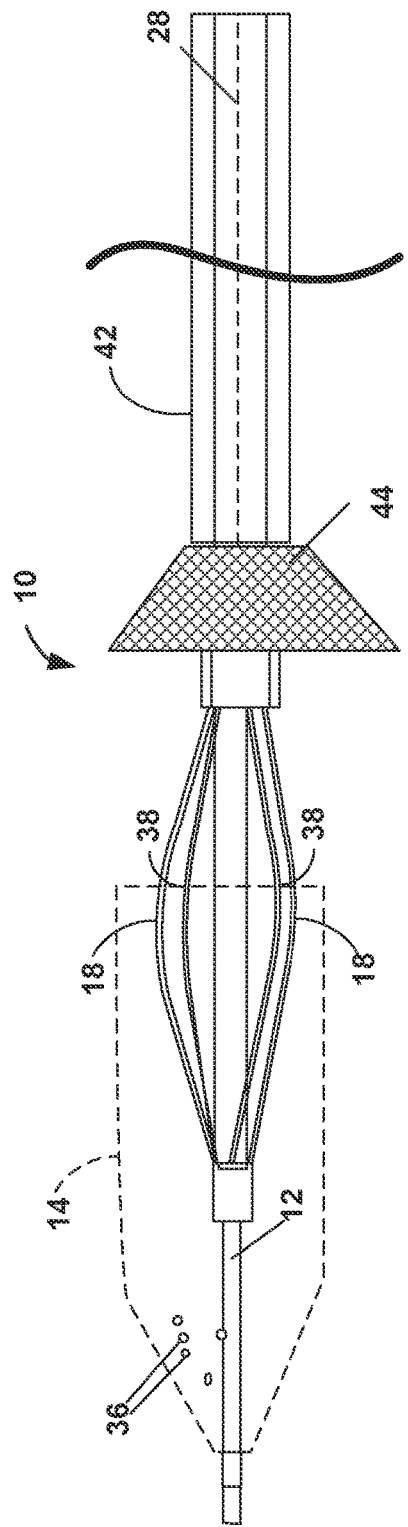
FIGS. 7A and 7B are conceptual diagrams depicting a method of collapsing a thrombus removal device from a deployed configuration to a delivery configuration.
Figure 7B:
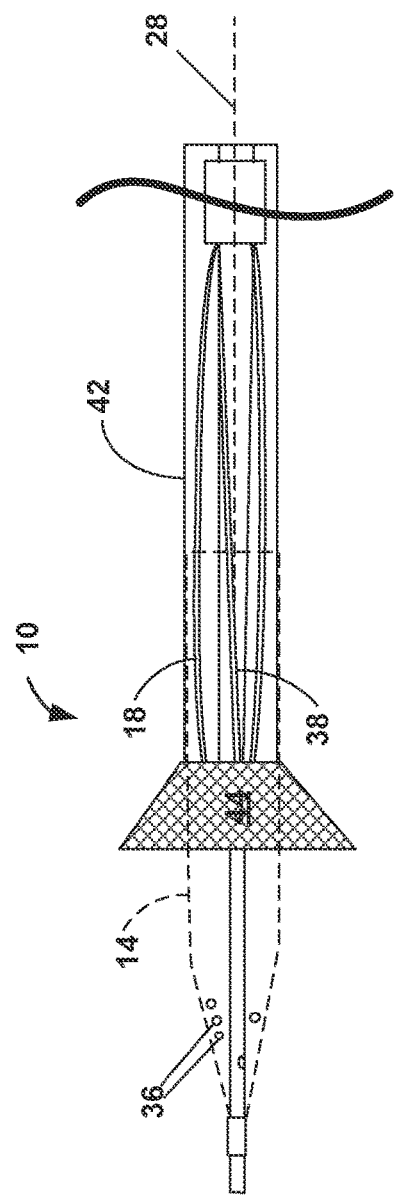

FIGS. 7A and 7B are conceptual diagrams depicting a method of collapsing an example thrombus removal device 10 from a deployed configuration to a delivery configuration. The expandable element 14 is shown in phantom lines in FIGS. 7A and 7B to better show the stationary element 18 and the movable element 38. FIG. 7A depicts the stationary element 18 and the movable element 38 in a partially-deployed (e.g., partially expanded) configuration, in which a central portion of the stationary element 18 and the movable element 38 expanded spread radially outward from an elongated expandable element support structure 12. Similarly, the expandable element 14 is in a deployed configuration so as to define a basket shape having an open internal volume configured to receive and/or collect portions of a thrombus.

In the example shown in FIG. 7B, the stationary element 18 and the movable element 38 have been collapsed radially inward from the deployed configuration to a delivery configuration (e.g., a collapsed or contracted state). For example, the thrombus removal device 10 may include a pull wire or other mechanism (not shown) configured to convert the thrombus removal device 10 between the delivery configuration and the deployed configuration. In some examples, each of the expandable element 14, the stationary element 18, and the movable element 38 may include a separate or distinct pull member or other user-input mechanism configured to cause the respective element to convert between the delivery configuration and the deployed (expanded) configuration. In some examples, a manual expansion mechanism may enable or enhance outward radial support to the expandable element 14 and stationary element 18 while the physician pulls them proximally through a thrombus, preventing the thrombus from causing them to collapse radially inward while segmenting and macerating the thrombus.

In other examples, each of the expandable element 14, the stationary element 18, and the movable element 38 are configured to self-expand when extended outward from a delivery catheter, and configured to contract to a more compressed configuration under the compression force applied by the retrieval catheter 42 (e.g., the funnel 44 of the retrieval catheter 42) when proximally withdrawn back into the retrieval catheter 42. The more compressed configuration may be referred to as a "delivery" configuration, although the thrombus removal device may have a different maximum cross-sectional dimension during delivery via the delivery catheter and retrieval via the retrieval catheter 42. While in the delivery configuration shown in FIG. 7B, the stationary element 18 and the movable element 38 both define a maximum cross-sectional dimension (the cross section taken in a direction transverse to the longitudinal axis 28) that is sufficiently small to enable the stationary element 18 and the movable element 38 to be proximally withdrawn into the retrieval catheter 42. Similarly, expandable element 14 may be collapsed from a deployed configuration to a delivery configuration and may be proximally withdrawn into the retrieval catheter 42 in order to remove any captured thrombus portions from the body of the patient.

Figure 8A:
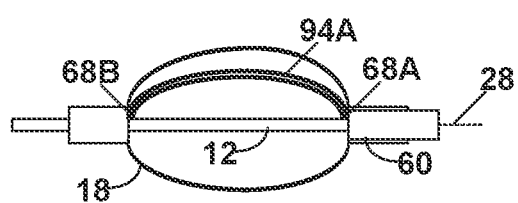
FIGS. 8A-8E depict five example configurations of a movable element of a thrombus removal device.

The movable arms of a movable element, including movable element 38 of FIGS. 1 and 2, may have any suitable configuration. FIGS. 8A-8E depict example configurations of a movable element of a thrombus removal device. More specifically, FIGS. 8A-8E each depict a different example shape of one or more elongated arms, which may each be examples of an elongated arm 86A of FIG. 5. For example, FIG. 8A depicts an elongated arm 94A that has a parabolic shape while in a deployed configuration. Proximal end 68A and distal end 68B of elongated arm 94A may be generally longitudinally aligned along a direction parallel to the central longitudinal axis 28 of the elongated expandable element support structure 12, or may be slightly offset such that the elongated arm 94A extends across a small portion of the circumference of the elongated expandable element support structure 12.

Figure 8B:
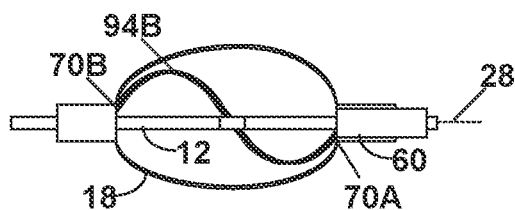

FIG. 8B depicts another example elongated arm 94B that has a sinusoidal shape while in a deployed configuration. Proximal end 70A and distal end 70B of the elongated arm 94B may be generally longitudinally aligned along a direction parallel to the central longitudinal axis 28 of the elongated expandable element support structure 12, or may be slightly offset such that the elongated arm 94B extends across a small portion of the circumference of the elongated expandable element support structure 12.

Figure 8C:
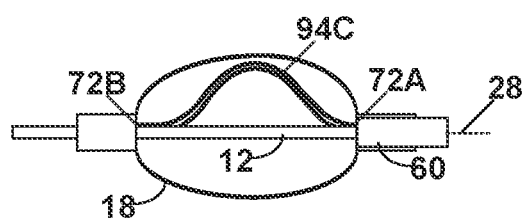

FIG. 8C depicts an example elongated arm 94C that defines a bell-curve shape while in a deployed configuration. Proximal end 72A and distal end 72B of the elongated arm 94C may be generally longitudinally aligned along a direction parallel to the central longitudinal axis 28 of the elongated expandable element support structure 12, or may be slightly offset such that the elongated arm 94B extends across a small portion of the circumference of the elongated expandable element support structure 12.

Figure 8D:
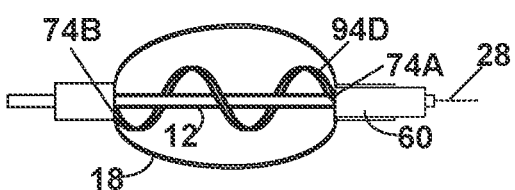

FIG. 8D depicts an example elongated arm 94D that defines a helical shape that wraps circumferentially around the longitudinal axis 28 while in a deployed configuration (similar to the elongated arms 86A-86C of the movable element 86 of FIG. 4). Proximal end 74A and distal end 74B of the elongated arm 94D may be generally offset along a direction parallel to the central longitudinal axis 28 such that the elongated arm 94D extends completely around the complete circumference of the elongated expandable element support structure 12 at least a single time (e.g., at least one complete turn around the circumference).

Figure 8E:
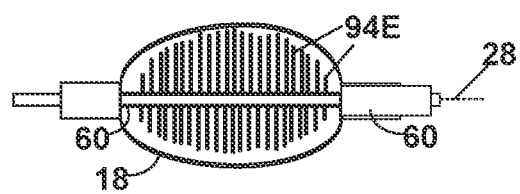

FIG. 8E depicts an example movable element having a plurality of elongated arms 94E that extend radially outward from central longitudinal axis 28 while in a deployed configuration. In the example of FIG. 8E, the movable element defines a brush-type structure, in which each of elongated arms 94E defines a respective bristle of the brush structure. Each of elongated arms 94E may be relatively flexible, and be attached at one end to a movable element support structure 60. Although shown in FIG. 8E as extending from only two sides of movable element support structure 60, in other examples, elongated arms 94E may be arranged around the entire circumference of movable element support structure 60. In some examples, but not all examples, movable element support structure 60 may be configured to rotate about central longitudinal axis 28, causing elongated arms 94E to similarly rotate about axis 28.

Figure 9A:
FIGS. 9A-9D depict four example surface textures of a movable element of a thrombus removal device.

In some examples, one or more of the elongated arms of the movable element and/or the stationary elements described herein may include different types of surface textures, which may impart different types of results to the maceration of a thrombus by the respective arm. FIGS. 9A-9D depict four example surface textures 96A-96D of a surface of at least one component of the thrombus removal device 10. More specifically, each of the example surface textures 96A-96D may include surface textures of one or more elongated arms of a movable element 38 (FIG. 1), a stationary element 18, or both. FIG. 9A depicts a first example surface texture 96A for an elongated arm of a thrombus removal device 10. The surface texture 96A is primarily smooth or planar, reducing an amount of contact (e.g., friction) between the respective elongated arm and a thrombus 36, which in some cases, may enable the elongated arm to slice more smoothly or easily through the thrombus 36 (e.g., cleave apart two distinct portions of the thrombus 36 while leaving the individual portions generally intact).

Figure 9B:
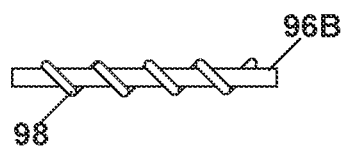

FIG. 9B depicts another example surface texture 96B for an elongated arm of a thrombus removal device 10. The surface texture 96B defines an "open pitch cable" surface, wherein an elongated wire 98 is loosely helically coiled around the respective elongated arm so as to define a gap in between each adjacent loops of the helical coil. The surface texture 96B may increase an amount of contact (e.g., friction) between the respective elongated arm and a thrombus 36, enabling the respective elongated arm to more easily macerate the thrombus 36 (e.g., cut a section of thrombus into a plurality of smaller portions or crush a more-solid thrombus portion into a less-viscous thrombus portion) for a given motion.

Figure 9C:
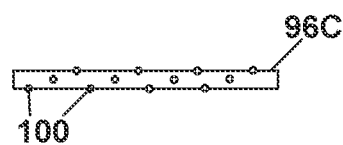

FIG. 9C depicts another example surface texture 96C, which defines a "bumpy" or "rough" surface, defining a plurality of protrusions 100. The surface texture 96C may increase an amount of contact (e.g., friction) between the respective elongated arm and a thrombus 36, enabling the respective elongated arm to more easily macerate the thrombus 36 for a given motion.

Figure 9D:
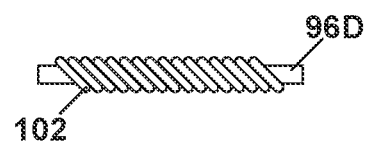

FIG. 9D depicts another example surface texture 96D for an elongated arm of a thrombus removal device 10. The surface texture 96D defines a "closed pitch cable" surface, wherein an elongated wire 102 is tightly helically coiled around the respective elongated arm such that adjacent loops of the helical coil are in physical contact (e.g., defining no gaps in between successive coil loops). The surface texture 96D may increase an amount of contact (e.g., friction) between the respective elongated arm and a thrombus 36, enabling the respective elongated arm to more easily macerate thrombus 36 for a given motion.

FIGS. 10A-10D depict four example motion configurations for a movable element 116A-116D of a respective thrombus removal device 118A-118D. The thrombus removal devices 118A-118D are each examples of the thrombus removal device 10 of FIG. 1, and the movable elements 116A-116D are each examples of the movable element 38 of FIG. 1.

Figure 10A:
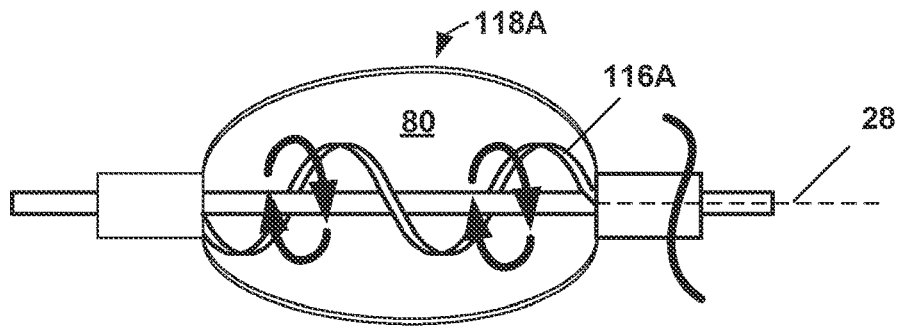
FIGS. 10A-10D depict four example motion configurations for a movable element of a thrombus removal device.

FIG. 10A depicts a first example movable element 116A. The movable element 116A includes a rotatable element configured to rotate about a central longitudinal axis 28 of the thrombus removal device 118A, as shown by the arrows in FIG. 10A. The actuator 66 (FIG. 1) may include variable speed settings, which a clinician may select based on the type of thrombus to be removed or other factors. For example, for an acute thrombus, the clinician may select a relatively lower speed setting, such as about 3000 revolutions per minute (rpm) to about 4999 rpm. For a subacute thrombus, which may be more dense than an acute thrombus, the clinician may select a medium speed setting, such as about 5000 rpm to about 6999 rpm. For a chronic thrombus, which may be more dense than an acute thrombus and a subacute thrombus, the clinician may select a relatively higher speed setting, such as about 7000 rpm to 10,000 rpm or more.

In some examples, the actuator 66 includes a user interface, such as a keypad, touchscreen, dial or any other suitable user-input mechanism that enables the clinician to customize the speed setting, such as anywhere from 0 rpm to about 10,000 rpm. The user interface can enable the clinician to select any speed setting in a predefined range or may be configured to provide a preset number of speed settings (e.g., five or fewer speed settings) from which the clinician can select.

In other examples, the actuator 66 may include only a binary on/off user-input mechanism, causing movable element 116A to either not rotate at all ("off") or rotate at a single speed setting ("on"), such as at about 6000 rpm. In another example, while in the "on" configuration, the actuator 66 may cause movable element 116A to periodically "pulse" on and off, or to alternate or oscillate between a first rotational speed (e.g., about 2000 rpm) and a second rotational speed (e.g., about 7000 rpm).

In other examples, the actuator 66 includes a user-input mechanism enabling the rotatable element 116A to be manually rotated by a clinician, e.g., wherein a single user-input signal corresponds to a partial or complete rotation of the rotatable element 116A or where the clinician manually rotates the rotatable element 116A around the longitudinal axis 28 using the movable element support structure 60 or another structure. As one illustrative example, actuator 66 may include a mechanism including a trigger coupled to movable element support structure 60. In such examples, a user may apply pressure with a thumb or other finger to depress the trigger, causing the rotatable element 116A to rotate about the longitudinal axis 28.

Figure 10B:
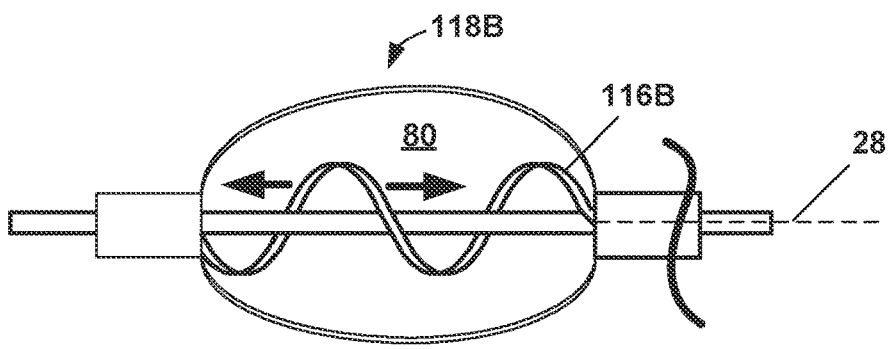

FIG. 10B depicts another example movable element 116B, which includes a plunging element configured to oscillate in a direction parallel to the central longitudinal axis 28 of the thrombus removal device 118B. The plunging element can include one or more helical coils, as shown in FIG. 10B. In some examples, the entire plunging element is configured to oscillate axially back-and-forth as a rigid unit, in which all of the one or more helical coils are configured to move the same direction at the same time, within the volume defined by the stationary element of the thrombus removal device 118B. In another example configuration, the plunging element 116B includes a coiled spring configured to axially compress and expand, in which two or more coils are configured to alternatingly move toward and away from each other, within the volume defined by the stationary element of the thrombus removal device 118B.

In some examples, the actuator 66 includes a motor or other control element configured to cause the plunging element 116B to automatically follow a plunging motion. In other examples, the actuator 66 includes a user-input mechanism enabling the plunging element 116B to be manually plunged by a clinician, e.g., wherein a single user-input signal corresponds to a single plunging oscillation of the plunging element 116B or where the clinician manually pushes the plunging element 116B back and forth along the longitudinal axis 28 using the movable element support structure 60 or another structure, such as a plunging tube disposed around the expandable member support structure.

Figure 10C:
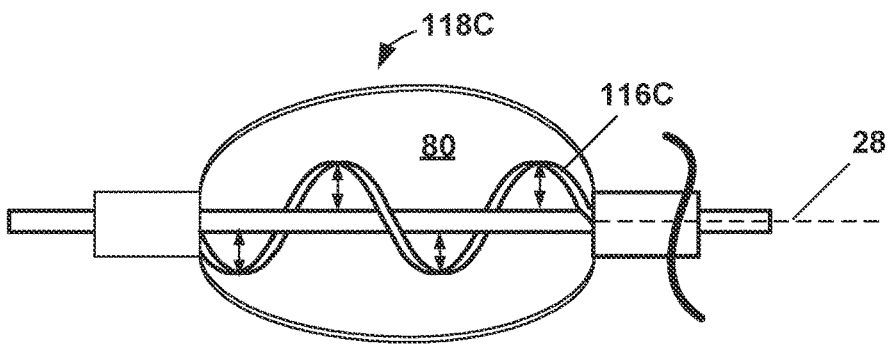

FIG. 10C depicts another example movable element 116C, which includes a vibrating element configured to vibrate at or near ultrasonic speeds relative to the central longitudinal axis 28 of the thrombus removal device 118C under the control of the actuator 66. The vibrating element 116C includes one or more portions configured to spread radially inward and outward from central longitudinal axis 28.

Figure 10D:
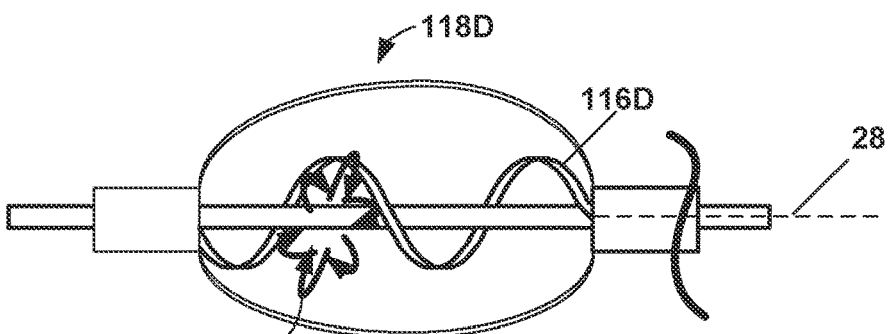

FIG. 10D depicts another example movable element 116D, which includes a combination vibrating-and-rotating element in which one or more portions of the movable element 116D are configured to move radially inward and outward from longitudinal axis 28 while also rotating about longitudinal axis 28, thereby tracing out a repetitive arc-pattern or flower-petal shape 76, as shown in FIG. 10D.

Figure 11:
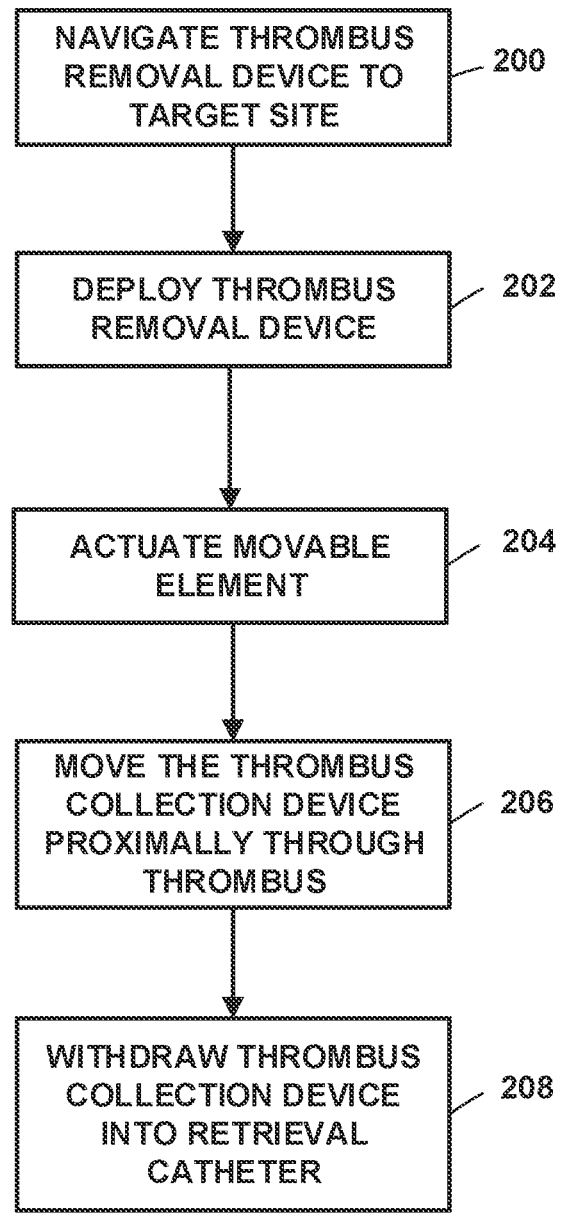
FIG. 11 is a flow diagram of an example method of removing a thrombus from vasculature of a patient using an example thrombus removal device described herein.

FIG. 11 is a flow diagram of an example method of removing a thrombus from vasculature of a patient using a thrombus removal device, such as the thrombus removal device 10 of FIG. 1. Although described with reference to thrombus removal device 10 of FIG. 1, the method of FIG. 11 may be used with other any suitable thrombus removal device described herein. A clinician may navigate the thrombus removal device 10 to a target site within a patient (200), which can be, for example, in a blood vessel. For example, the clinician may deliver the thrombus removal device 10 to a target site with the aid of a delivery catheter 40 (FIG. 4). The clinician may position the thrombus removal device 10 on a distal side of a thrombus 36, as described with reference to FIG. 2, and deploy the expandable element 14, the stationary element 18, and the movable element 38 into their respective deployed configurations (202).

The clinician may then, with the aid of the actuator device 66, cause the movable element 38 to move relative to the stationary element 18 (204). For example, the actuator 66 may be configured to cause the movable element 38 to move according to a predetermined motion pattern, such as a rotational pattern, a plunging pattern, or a vibrational pattern. The clinician may then proximally withdraw the thrombus removal device 10, e.g., the expandable element 14, the stationary element 18 and the movable element 38 as the movable element 38 is moving relative to the stationary element 18, through the thrombus 36 (206) to segment and macerate the thrombus 36 into smaller pieces. The macerated portions of thrombus 36 are collected in the basket 22 of the expandable element 14 as the clinician proximally withdraws the thrombus removal device 10 from the patient (in a direction towards the clinician). After collecting at least part of the thrombus 36 in the basket 22, the clinician may remove the collected parts of the thrombus 36 and the thrombus removal device 10 from the patient (208), e.g., with the aid of a retrieval catheter 42. In some examples, the clinician may clean the collected thrombus 36 from the basket 22 and reintroduce the thrombus removal device 10 into the vasculature of the patient and repeat the method shown in FIG. 11 one or more times.

Various examples have been described. These and other examples are within the scope of the following claims.

What is claimed is:

1. A medical device comprising:
   an elongated support member;
   an expandable element disposed on the elongated support member;
   a stationary element comprising a first plurality of arms;
   a proximal end cap on the elongated support member, wherein each arm of the first plurality of arms extends at least between a proximal portion of the expandable element and the elongated support member, wherein a proximal end of each arm of the first plurality of arms is directly coupled to the elongated support member via the proximal end cap, wherein the first plurality of arms is configured to segment a thrombus into smaller pieces as the thrombus moves through the stationary element, wherein the expandable element is configured to capture at least some of the smaller pieces, wherein the first plurality of arms is configured to self-expand radially outward relative to the elongated support member, and wherein the proximal end of each arm of the first plurality of arms is positioned between proximal and distal ends of the elongated support member such that when the elongated support member, the expandable element, and the stationary element are positioned in a blood vessel in which the thrombus is located, the proximal end of each arm of the first plurality of arms is configured to be positioned distal to at least a portion of the thrombus;
   a movable element disposed radially inward from the stationary element, the movable element configured to move relative to the stationary element to macerate the thrombus as the thrombus moves through the stationary element, wherein the movable element comprises a second plurality of arms extending generally along the elongated support member; and
   a movable element support structure on the elongated support member, wherein a proximal end of each arm of the second plurality of arms is rotatably coupled to the elongated support member via the movable element support structure, and wherein the proximal end cap and the movable element support structure are at least partially coextensive along the elongated support member, wherein the movable element comprises a rotatable element, wherein the medical device further comprises a rotatable tube disposed around the elongated support member, and wherein the rotatable element is coupled to the rotatable tube and is configured to rotate about a longitudinal axis of the elongated support member to rotate the rotatable element relative to the stationary element.

2. The medical device of claim 1, wherein the movable element is configured to expand radially outward from a delivery configuration to a deployed configuration, and wherein the movable element is configured to move within a volume defined by the stationary element.

3. The medical device of claim 1, wherein the rotatable element is configured to oscillate between a first rotational speed and a second rotational speed.

4. The medical device of claim 1, wherein the movable element comprises a vibrating element configured to oscillate radially inward and outward relative to the stationary element.

5. The medical device of claim 1, wherein the expandable element defines an elongated basket that tapers in a distal direction.

6. The medical device of claim 1, wherein the movable element defines a generally smooth surface.

7. The medical device of claim 1, wherein the movable element defines a surface having a plurality of protrusions.

8. The medical device of claim 1, wherein the expandable element comprises an expandable stent.

9. The medical device of claim 1, wherein the stationary element is configured to self-expand radially outward relative to the elongated support member.

10. The medical device of claim 1, wherein the elongated support member defines a plurality of openings configured to release a lytic agent to dissolve the thrombus.

11. The medical device of claim 1, further comprising an elongated wire configured to cause the movable element to expand or contract.

12. The medical device of claim 1, wherein each arm of the first plurality of arms comprises nitinol.

13. The medical device of claim 1, further comprising a proximal ring at a proximal portion of the expandable element, the proximal ring configured to expand radially outward.

14. The medical device of claim 1, wherein a length of the stationary element is 50 mm to 150 mm, the length measured from a proximal-most end of the stationary element to a distal-most end of the stationary element.

15. The medical device of claim 1, wherein the stationary element has a biasing force radially outward relative to the elongated support member.

16. A system comprising:
the medical device of claim 1, and
a retrieval catheter defining a retrieval catheter lumen and including a funnel at a distal portion of the retrieval catheter; the funnel configured to compress at least the stationary element and the movable element when the medical device is withdrawn proximally into the retrieval catheter lumen.

17. A method comprising using a medical device to macerate a thrombus, wherein the medical device comprises:
an elongated support member;
an expandable element disposed on the elongated support member, wherein the elongated support member is positioned generally along a longitudinal axis extending from a proximal end of the expandable element to a distal end of the expandable element, and wherein the distal end of the expandable element is slidably coupled to the elongated support member;
a stationary element comprising a first plurality of arms;
a proximal end cap on the elongated support member, wherein each arm of the first plurality of arms extends at least between a proximal portion of the expandable element and the elongated support member, wherein a proximal end of each arm of the first plurality of arms is directly coupled to the elongated support member via the proximal end cap, wherein the first plurality of arms is configured to segment a thrombus into smaller pieces as the thrombus moves through the stationary element, wherein the first plurality of arms is configured to self-expand radially outward relative to the elongated support member, wherein the expandable element is configured to capture at least some of the smaller pieces, and wherein the proximal end of each arm of the first plurality of arms is positioned between proximal and distal ends of the elongated support member such that when the elongated support member, the expandable element, and the stationary element are positioned in a blood vessel in which the thrombus is located, the proximal end of each arm of the first plurality of arms is configured to be positioned distal to at least a portion of the thrombus;
a movable element disposed radially inward from the stationary element, the movable element configured to move relative to the stationary element to macerate the thrombus as the thrombus moves through the stationary element, wherein the movable element comprises a second plurality of arms extending generally along the elongated support member; and
a movable element support structure on the elongated support member, wherein a proximal end of each arm of the second plurality of arms is rotatably coupled to the elongated support member via the movable element support structure, and wherein the proximal end cap and the movable element support structure are at least partially coextensive along the elongated support member, wherein the movable element comprises a rotatable element, wherein the medical device further comprises a rotatable tube disposed around the elongated support member, and wherein the rotatable element is coupled to the rotatable tube and is configured to rotate about a longitudinal axis of the elongated support member to rotate the rotatable element relative to the stationary element.

18. The method of claim 17, wherein using the medical device to macerate the thrombus comprises:
navigating the medical device to a target site within vasculature of a patient;
deploying the medical device from a delivery configuration to a deployed configuration, wherein the first plurality of arms is self-expanded in the deployed configuration of the medical device;
moving the medical device proximally through the thrombus while actuating a motion of the movable element; and
withdrawing the medical device into a retrieval catheter.

19. A medical device comprising:
an elongated support member;
an expandable element disposed on the elongated support member;

a stationary element comprising a first plurality of arms;
a proximal end cap on the elongated support member, wherein each arm of the first plurality of arms extends at least between a proximal portion of the expandable element and the elongated support member, wherein a proximal end of each arm of the first plurality of arms is directly coupled to the elongated support member via the proximal end cap, wherein the first plurality of arms is configured to segment a thrombus into smaller pieces as the thrombus moves through the stationary element, wherein the expandable element is configured to capture at least some of the smaller pieces, wherein the first plurality of arms is configured to self-expand radially outward relative to the elongated support member, and wherein the proximal end of each arm of the first plurality of arms is positioned between proximal and distal ends of the elongated support member such that when the elongated support member, the expandable element, and the stationary element are positioned in a blood vessel in which the thrombus is located, the proximal end of each arm of the first plurality of arms is configured to be positioned distal to at least a portion of the thrombus;
a movable element disposed radially inward from the stationary element, the movable element configured to move relative to the stationary element to macerate the thrombus as the thrombus moves through the stationary element, wherein the movable element comprises a second plurality of arms extending generally along the elongated support member; and
a movable element support structure on the elongated support member, wherein a proximal end of each arm of the second plurality of arms is rotatably coupled to the elongated support member via the movable element support structure, and wherein the proximal end cap and the movable element support structure are at least partially coextensive along the elongated support member,
wherein the medical device further comprises a rotatable tube disposed around the elongated support member, and wherein the rotatable tube is coupled to a distal end of each arm of the second plurality of arms, the rotatable tube being configured to rotate about a longitudinal axis of the elongated support member to rotate the movable element relative to the stationary element.

20. The medical device of claim 19, wherein the rotatable tube defines a plurality of slots, each of the plurality of slots being configured to receive and retain a respective arm of the second plurality of arms.

* * * * *